(12) United States Patent
Xian et al.

(10) Patent No.: US 12,279,858 B2
(45) Date of Patent: Apr. 22, 2025

(54) SELF-CONTAINED WEARABLE METABOLIC ANALYZER

(71) Applicant: TF HEALTH CORP., Tempe, AZ (US)

(72) Inventors: Xiaojun Xian, Chandler, AZ (US); Devon Bridgeman, Mesa, AZ (US); Francis Tsow, Tampa, FL (US); Erica Forzani, Mesa, AZ (US); Nongjian Tao, Fountain Hills, AZ (US)

(73) Assignee: TF HEALTH CORP., Tempe, AZ (US)

( * ) Notice: Subject to any disclaimer, the term of this patent is extended or adjusted under 35 U.S.C. 154(b) by 1050 days.

(21) Appl. No.: 17/283,768

(22) PCT Filed: Oct. 8, 2019

(86) PCT No.: PCT/US2019/055235
§ 371 (c)(1),
(2) Date: Apr. 8, 2021

(87) PCT Pub. No.: WO2020/076855
PCT Pub. Date: Apr. 16, 2020

(65) Prior Publication Data
US 2021/0378546 A1 Dec. 9, 2021

Related U.S. Application Data

(60) Provisional application No. 62/743,417, filed on Oct. 9, 2018.

(51) Int. Cl.
*A61B 5/083* (2006.01)
*A61B 5/00* (2006.01)
(Continued)

(52) U.S. Cl.
CPC .......... *A61B 5/0836* (2013.01); *A61B 5/0002* (2013.01); *A61B 5/0833* (2013.01);
(Continued)

(58) Field of Classification Search
None
See application file for complete search history.

(56) References Cited

U.S. PATENT DOCUMENTS 4,875,477 A   10/1989   Waschke et al.
6,899,683 B2   5/2005   Mault et al.
(Continued)

FOREIGN PATENT DOCUMENTS

WO   2017177340 A1   10/2017

OTHER PUBLICATIONS

International Preliminary Report on Patentability for International Patent Application No. PCT/US2019/055235, mailed Apr. 22, 2021, 12 pages.
(Continued)

*Primary Examiner* — Jay B Shah
(74) *Attorney, Agent, or Firm* — Withrow + Terranova, PLLC; Vincent K. Gustafson

(57) ABSTRACT

A stand-alone, fully integrated self-contained wearable metabolic analyzer for metabolic rate and respiratory quotient measurement. It includes a device body, disposable mask, and headgear. The device body comprises multiple different miniaturized modules, including a colorimetric sensing module, flow module, control circuit, power module, environmental sensors, wireless module, communication module, memory module, signal processing module, and display module. A disposable sensor chip, coated with chemical sensing probes, is utilized in the colorimetric sensing module for breath O2 and CO2 detection. A Venturi tube and pressure sensor-based flow module measures breath flow rate. The self-contained wearable metabolic analyzer derives physiological parameters including resting energy expenditure (REE), respiratory quotient (RQ), oxygen consumption (VO2), carbon dioxide production
(Continued)

(VCO2), minute ventilation (VE), breath frequency (BF), and tidal volume (TV) from the measurement.

20 Claims, 22 Drawing Sheets

(51) Int. Cl.
*A61B 5/097* (2006.01)
*G01N 21/25* (2006.01)
*G01N 21/31* (2006.01)
*G01N 33/497* (2006.01)

(52) U.S. Cl.
CPC ............ *A61B 5/097* (2013.01); *A61B 5/6803* (2013.01); *G01N 21/251* (2013.01); *G01N 21/31* (2013.01); *G01N 33/497* (2013.01); *A61B 2560/0252* (2013.01); *A61B 2560/0257* (2013.01); *A61B 2562/0247* (2013.01); *A61B 2562/029* (2013.01); *G01N 2021/3129* (2013.01); *G01N 33/4975* (2024.05)

(56) References Cited

U.S. PATENT DOCUMENTS

| | | |
|---|---|---|
| 7,204,250 B1 | 4/2007 | Burton |
| 7,575,005 B2 | 8/2009 | Mumford et al. |
| 10,078,074 B2 | 9/2018 | Tsow et al. |
| 2003/0028120 A1 | 2/2003 | Mault et al. |
| 2006/0150977 A1 | 7/2006 | Flabouris |
| 2006/0201503 A1* | 9/2006 | Breen ............... A61M 16/0875 128/204.22 |
| 2007/0107728 A1 | 5/2007 | Ricciardelli et al. |
| 2009/0227887 A1 | 9/2009 | Howard et al. |
| 2013/0150746 A1 | 6/2013 | Tao et al. |
| 2013/0173713 A1 | 7/2013 | Anderson et al. |
| 2014/0275857 A1 | 9/2014 | Toth et al. |
| 2017/0324390 A1* | 11/2017 | Wheatley ............... H03G 9/025 |
| 2018/0326173 A1* | 11/2018 | Ewers ............... A61M 16/0666 |
| 2019/0110714 A1* | 4/2019 | O'Brien ................. A61B 5/091 |

OTHER PUBLICATIONS

First Office Action for Chinese Patent Application No. 201980081705.1, mailed Jan. 9, 2024, 12 pages.
International Search Report (Form PCT/ISA/210) for International Application No. PCT/US2019/055235 mailed Dec. 20, 2019, 3 pages.
Written Opinion (Form PCT/ISA/237) for International Application No. PCT/US2019/055235 mailed Dec. 20, 2019, 10 pages.
Examination Report for European Patent Application No. 19870184.9, mailed Mar. 15, 2023, 5 pages.
Extended European Search Report for European Patent Application No. 19870184.9, mailed Nov. 18, 2021, 8 pages.
Second Office Action for Chinese Patent Application No. 201980081705.1, mailed Aug. 30, 2024, 22 pages.

* cited by examiner

QR code sensor chip

SELF-CONTAINED WEARABLE METABOLIC ANALYZER

CROSS-REFERENCE TO RELATED APPLICATION(S)

This application is a 35 U.S.C. § 371 national phase filing of International Application No. PCT/US2019/055235 filed on Oct. 8, 2019, and further claims priority to U.S. Provisional Patent Application No. 62/743,417 filed on Oct. 9, 2018, wherein the entire disclosures of the foregoing applications are hereby incorporated by reference herein.

TECHNICAL FIELD

The present disclosure is directed to a wearable, stand-alone, and fully integrated metabolic analyzer for indirect calorimetry-based metabolic rate and respiratory quotient measurement.

BACKGROUND

Significance for Metabolic Rate Measurement

Resting metabolic rate contributes up to 80% of the total energy expenditure of a human. It plays a very important role in determining the energy balance of the human body. It has wide applications in weight loss, nutrition, fitness, and chronic disease management. Although equations, such as the Harris-Benedict equation and the Mifflin-St. Jeor equation, have been used to calculate the resting metabolic rate based on weight, height, gender, and age of the user, it is an estimation based on demographic average rather than an accurate measurement for the individual, which has errors greater than 50%. For better health outcome and more efficient weight control, an apparatus for accurate and reliable measurement of an individual's metabolic rate is needed. In addition to metabolic rate, respiratory quotient (RQ) is another useful parameter to assess the body flexibility to oxidize fatty acid and/or carbohydrates, which can be altered in different chronic diseases such as diabetes, hypothyroidism, and metabolic syndromes. RQ indicates the energy source, which cannot be estimated from equation, but can be determined from measurement based on indirect calorimetry, described below.

Indirect Calorimetry as Gold Standard for Metabolic Rate Measurement

There are two generally accepted ways to measure a person's metabolic rate: direct calorimetry and indirect calorimetry. The former requires the person to stay in a closed chamber with controlled environmental for 24 hours while monitoring the heat generation, from which the metabolic rate is determined. This is an accurate way to measure metabolic rate, but it is no longer used due to practical reasons. The latter determines the metabolic rate by measuring the oxygen consumption and carbon dioxide production rates from breath analysis. The indirect calorimetry can also determine the person's RQ from the ratio of carbon dioxide production and oxygen consumption. The measured parameters are used together with Weir Equation to calculate the metabolic rate, which has been widely used for non-invasive and accurate metabolic rate, and it remains a gold standard in measuring energy expenditure in the clinical settings.

Current Metabolic Analyzers Based on Indirect Calorimetry

To measure metabolic rate and RQ with indirect calorimetry, sensors are used to measure the breath oxygen and carbon dioxide concentrations as well as the breath flow rate. Some examples of widely used metabolic analyzers include metabolic carts, such as Ultima CCM™ indirect calorimeter from MGC Diagnostics, Oxycon from Carefusion and Parvo Medics TrueOne 2400 from Parvo Medics. While usually accurate and reliable, these devices are bulky, expensive, and require dedicated personnel to operate, calibrate, and maintain. As such, these devices are suitable only for use in hospitals and research institutes. To address the need for use in small clinics, fitness or weight-loss clubs, as well as for end consumers, several portable metabolic analyzers have been introduced to the market, including desktop devices, such as Fitmate devices from Cosmed, REEVUE devices from Korr and handheld devices, such as Medgem devices from Microlife, Lumen devices from Metaflow, and Breezing™ devices from TF Health Co.

In addition, other portable indirect calorimeters have been developed for assessment of energy expenditure and lactate threshold during exercise via the use of a face mask attached to apparatus capable to measure oxygen consumption rate and carbon dioxide production rate. The apparatus is attached onto the body with straps holding the instrument, which is connected to the face mask inlet and outlet extracting a portion of the inhaled or exhaled breath. Examples of this system are: wearable devices K4b and K5 from Cosmed, Oxycon Mobile form Carefusion, and TurboTrainer from Vacumed.

Need for a Self-Contained Wearable Metabolic Analyzer

The metabolic carts and portable metabolic analyzers described above address certain needs of metabolic rate measurement, but they are expensive, complex and difficult to use in the user's home or in low-resource settings. There is a need for a simple, convenient, user-friendly, and cost-effective metabolic rate measurement apparatus. The present disclosure addresses this need with an innovative wearable technology for metabolic rate and RQ measurements by providing a new product design with technological breakthroughs.

Using a Mask as a Platform for Physiological Parameters Measurement

Traditionally, masks are used for athlete training, patient care, and environmental protection. Recently, attempts have been made to introduce different sensors to the mask for physiological parameters monitoring. For example, a mask with built-in sensors is described in U.S. Pat. No. 4,875,477 for monitoring vital functions. These sensors include temperature sensor and heart rate monitor mounted on the inside of the mask for detecting vital functions of the wearer. A mask described in U.S. Pat. No. 7,204,250B1, issued Apr. 17, 2007 to Burton, includes other sensors, e.g., oximetry sensors, position sensor, leakage sensor, ECG sensor, and temperature sensor, for treating sleep disorders, breathing disorders, and anesthesia monitoring. This mask is connected to an external gas delivery system to adjust the gas delivery setting based on data from the sensors. In another example, U.S. Pat. No. 7,575,005B2 describes a mask assembly with integrated sensors for obstructive sleep apnea treatment using continuous positive air pressure (CPAP) from an external source.

Other examples include U.S. Pat. No. 6,899,683B2, issued May 31, 2005 to Mault et. al. disclosing a respiratory analyzer adapted to be attached on a person's face with a mask or via a mouthpiece and a nose clip by James Mault et. al. All the above-described masks have a limiting feature in common. Namely, they must be connected to external equipment in order to operate. As such, they are not self-contained, stand-alone devices, and as a result, they do not operate as an on-face self-contained wearable analyzer.

Another key missing element in most of the published teachings for portable indirect calorimeters for assessment of energy expenditure during exercise (such as the instruments from Cosmed, Vacumed, and Carefusion) is a practical design that addresses hygiene concerns. The mask as well as the connector to the instruments, usually a turbine sensor, have to be disinfected with special procedure and cleaning solutions after use, before the next user can use the calorimeter. This makes the use impractical and dampens the usability of the calorimeters.

Although some published teachings have considered some hygiene issues (e.g. U.S. Pat. No. 6,899,683B2), those devices rely on the use of a disposable mask liner with a hygiene barrier attached to a detection unit passing both inhaled and exhaled air. Although, as for example in the '683 patent, the disposable filter is apparently intended to provide a single-time use. Further, the filter disclosed does not assure blocking transmission of viruses. Viruses typically range from about 0.004 to about 0.1 microns in size and can be transmitted by breathing through liners such as Flitrete® liners by as manufactured by 3M Company of Minnesota, which has a capability to capture particles only as small as 0.3 microns in size.

Most recently, in order to achieve wearability, a wearable and stand-alone mask device sold under brand name $VO_2$ MASTER™ has been introduced for maximum oxygen consumption rate ($VO_2$ max) measurement. $VO_2$ max is also known as maximal oxygen uptake, which refers to the maximum amount of oxygen consumption a person can utilize during intense exercise. The $VO_2$ MASTER™ device as directed to exercise physiology rather than resting metabolic rate. It is not designed for nutrition, weight loss, and heath purposes. In terms of technologies, the $VO_2$ MASTER™ mask integrates an off-the-shelf galvanic $O_2$ sensor and flow sensor, which is intrinsically not expandable for more chemical analytes detection in breath. Since chemicals sensors are usually bulky and heavy, it is difficult to stack multiple chemical sensors in the same wearable system for RQ, REE, and other breath biomarkers measurement. Furthermore, the $VO_2$ MASTER™ mask is designed for a single user only and there is no disposable part to avoid cross contamination. This makes it unsuitable for fitness club or clinic settings, where the device may typically be used by different users or patients.

Historically, compromising hygiene with wearability and usability has been a challenge. In addition, achieving miniaturized indirect calorimeters with full wearability and simultaneous assessment of metabolic rate and respiratory quotient would require simultaneous analysis of oxygen and carbon dioxide in breath, together with temperature, humidity, and volume flow rate, in order to determine metabolic rate and RQ accurately.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

A self-contained wearable metabolic analysis apparatus is disclosed including a device body having an integrated colorimetric sensor chip for simultaneous oxygen and carbon dioxide measurement, and an integrated flow sensor module for flow rate measurement. A disposable mask is attached to the device body and is adapted to allow aseptic breathing where the user inhales from ambient air and exhales into the flow sensor module, from which a small portion of the user's breath is taken into the integrated chemical sensor module. Headgear is adapted to attach the device body on a user's head. A data transmission device is adapted for communication an external electronic device.

BRIEF DESCRIPTION OF THE DRAWINGS

While the novel features of certain embodiments of the invention are set forth with particularity in the appended claims, the invention, both as to organization and content, will be better understood and appreciated, along with other objects and features thereof, from the following detailed description taken in conjunction with the drawings, in which:

DETAILED DESCRIPTION

Overall Description of a Self-Contained Wearable Metabolic Analyzer:

The foregoing description and drawings are of example embodiments of the intention and any changes and modifications may be made without departing from the concept, spirit, and scope of this disclosure as stated in the following claims.

Prior patents and applications by some of the inventors herein, and published as US2013/0150746 A1 (allowed), published Jun. 13, 2013 and U.S. Pat. No. 10,078,074 to Tsow et al. issued Sep. 18, 2018 address the above challenges by disclosing a portable metabolic analyzer system and a single integrated colorimetric sensor chip, each consisting of $CO_2$ and $O_2$ sensing elements. US2013/0150746 A1 (allowed) and U.S. Pat. No. 10,078,074 are incorporated herein by reference. The present disclosure offers several important changes from both the technology and user interface perspectives.

In terms of chemical sensing technology, an integrated and modular chemical sensing unit has been introduced in the new design disclosed herein, which enables the $O_2$ and $CO_2$ detection from partial breath instead of entire breath exposure. This improvement makes the colorimetric sensing module easy to configure and increases the lifetime of sensor from 2 minutes to more than 10 minutes. The new design uses Venturi-tube based flow sensing technology, which significantly reduces the backpressure without sacrificing the accuracy. More environmental sensors such as barometer, humidity sensor, and gyroscope are used to compensate the environmental factors that may affect the measurement itself, and to adapt for user comfort, which is needed to assure the true measurement of resting metabolic rate. In terms of user interface, different from the handheld device which only allows breath collection from the mouth, a face-worn design promotes natural breathing from both mouth and nose of the user, which is essential for the accurate measurement of REE.

Figure 1:
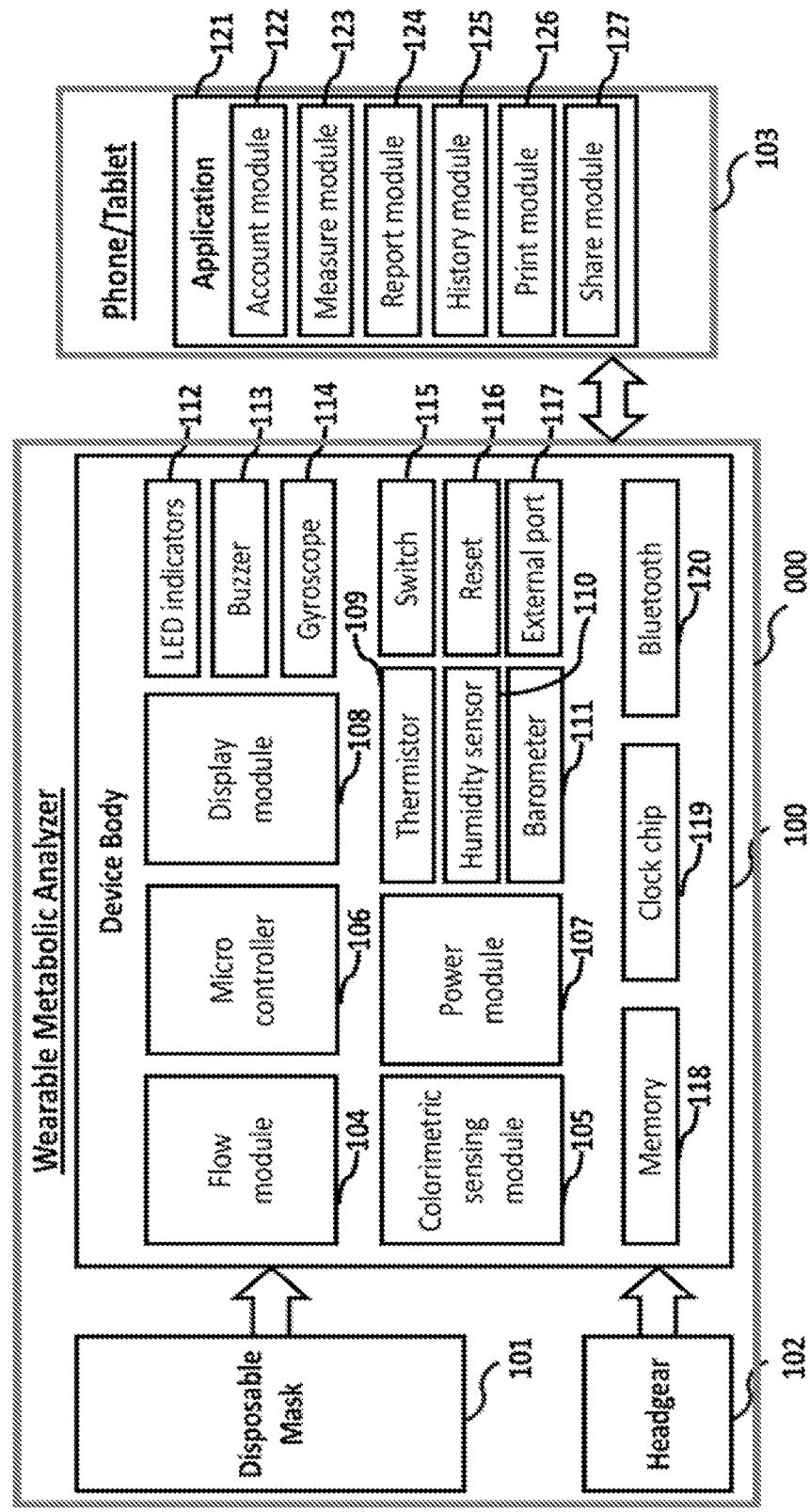
FIG. 1 is a block diagram illustrating an example of a self-contained wearable metabolic analyzer.

Referring now to FIG. 1, a block diagram illustrating an example of a self-contained, wearable, integrated, and stand-alone metabolic analyzer. A plurality of components in this embodiment of a self-contained wearable metabolic analyzer 1 include a device body 100, a disposable mask 101, headgear 102, and a phone/tablet/computer 103. Device body 100 may advantageously be an integrated unit consisting of mechanical parts, electronic circuit, and sensors, which provides the functions of breath flow rate measurement, and breath $O_2$ and $CO_2$ concentration detection. Disposable mask 101 is the breath collection unit made from mechanical parts, which covers the nose and mouth of the user with air-tight sealing and guides all the exhaled breath into device body 100 for breath chemical analysis, temperature, humidity, and flow rate measurements. Headgear 102 is a set of fabric ribbons with hook-and-loop fasteners, which keeps the assembled device body 100 and the disposable mask 101 around the user's head during the measurement. The phone/tablet/computer 103 is installed with an app 121, which connects with device body 100 for data communication and data management, where the app 121 consists of the following modules:

1) Account module 122: allowing user to create, manage, delete account and edit user profile;
2) Measure module 123: functions including data transmission between device body and phone/tablet/computer, guiding the user to perform the measurement, indicating the measurement progress and accessories such as QR code scanning;
3) Report module 124: displaying the final test results, including REE, RQ, $VO_2$, $VCO_2$, VE, BF, and TV; and generating a test report;
4) History module 125: storing, managing, and displaying the history of test results;
5) Print module 126: wirelessly communicating with external printer to print test report;
6) Data sharing module 127: allowing sharing the test results with others, such as doctors, professionals, family members, friends via email, text message, social media, or other health platforms.

In some embodiments, device body 100 and disposable mask 101 are integrated or merged into one unit. This merge does not substantially affect the functions of a self-contained wearable metabolic analyzer for metabolic rate measurement and breath analysis. However, disinfection and cleaning procedures can be implemented to clean the mask and flow channels to avoid any hygiene issues. To ensure a tight sealing between the mask and the user's face to avoid leakage during the metabolic rate measurement, the following design features could be applied: 1) apply ergonomic design to device body and its mask to conform the contour of the user's face features; 2) implement flexible materials, such as silicone rubber, along the fringe of the mask to provide air-tight sealing when mask is worn; 3) provide different sizes of mask for the user to choose; 4) make sure the inhalation and exhalation channels have big enough openings for less-resistive breathing.

Device body 100 is the measurement unit fully integrated with mechanical parts, electronic circuit and sensors for both breath flow and breath $O_2$ and $CO_2$ detection. In one example, the a plurality of modules and components are integrated together including a flow module 104, a colorimetric sensing module 105, a microcontroller 106, a power module 107, a display module 108, a thermistor 109, a humidity sensor 110, a barometer 111, a plurality of LED indicators 112, a buzzer 113, a gyroscope 114, a switch 115, a reset 116, an external port 117, a memory 118, a clock chip 119, and a transmission device 120 such as, for example, a Bluetooth® module.

Flow module 104 monitors the flow profile of the user during the measurement. Real-time breath flow rate is monitored by flow module 104, from which the breath frequency, tidal volume, and minute ventilation (VE) are determined after data processing. VE is a critical parameter for resting energy expenditure (REE) measurement. In the traditional Douglas Bag method, the user is asked to exhale into a bag to determine VE. Once the bag is full, the volume of the exhaled breath and the time duration for the user to fill up the bag are determined, from which VE is calculated and converted into STP (standard temperature and pressure) condition. Douglas Bag method is bulky, slow, and not easy to operate. Most of the commercial instruments for metabolic rate measurement use flow sensors to monitor real-time flow rate and integrate exhalation flow rate over time to calculate the total volume and determine VE.

Fast, continuous, and accurate monitoring of breath flow rate is desirable to precisely and reliably measure VE. There are at least three generally acceptable ways to measure breath flow rate. A first method uses a turbine flow meter. In a turbine flow meter, gas (e.g., breath) flows over a turbine rotor and force the rotor to rotate, with rotation speed proportional to the gas flow rate. By monitoring the rotation speed of the motor via an optical, electrical, or magnetic readout, the gas flow rate is determined. This method can cover a large flow rate range with relatively small back pressures at high exhalation flow rates, but the accuracy and response time are compromised because of the inertia of the rotor. The turbine flow meter can also get contaminated after long time breath exposure, which creates both accuracy and hygiene issues.

Another method for breath flow rate measurement uses an ultrasonic flow meter. An ultrasonic flow meter measures the gas flow rate by detecting the frequency shift of an ultrasonic wave transmitted through flowing gas due to the Doppler effect. The ultrasonic flow meter is reliable and requires less maintenance, but it is expensive and prone to temperature variation.

Yet another method uses a differential pressure Pneumotach approach. In this approach, the gas passes through a fixed orifice or a screen, through which a pressure difference is created. This pressure difference is correlated with the gas volume flow rate. By measuring the differential pressure with a pressure sensor, the breath flow rate can be determined. This is a simple, fast-response, and cost-effective way for breath flow rate measurement. Furthermore, because no gas passes through the pressure sensor during the measurement, breath condensation and contamination are of minimal issues, which, otherwise, could affect the stability and accuracy of the sensor. This method has been widely used for respiratory applications, such as spirometers, metabolic carts, and other clinical applications. Since a MEMS-based pressure sensor can be very small in size, if the orifice is carefully designed, the entire flow rate measurement module can be miniaturized for breath flow rate measurement. For these reasons, the Pneumotach approach is a preferred technology for breath analysis. However, the key is to find an optimal way to implement the flow rate measurement module in order to fit into a self-contained wearable metabolic analyzer, which is disclosed here.

Figure 2:
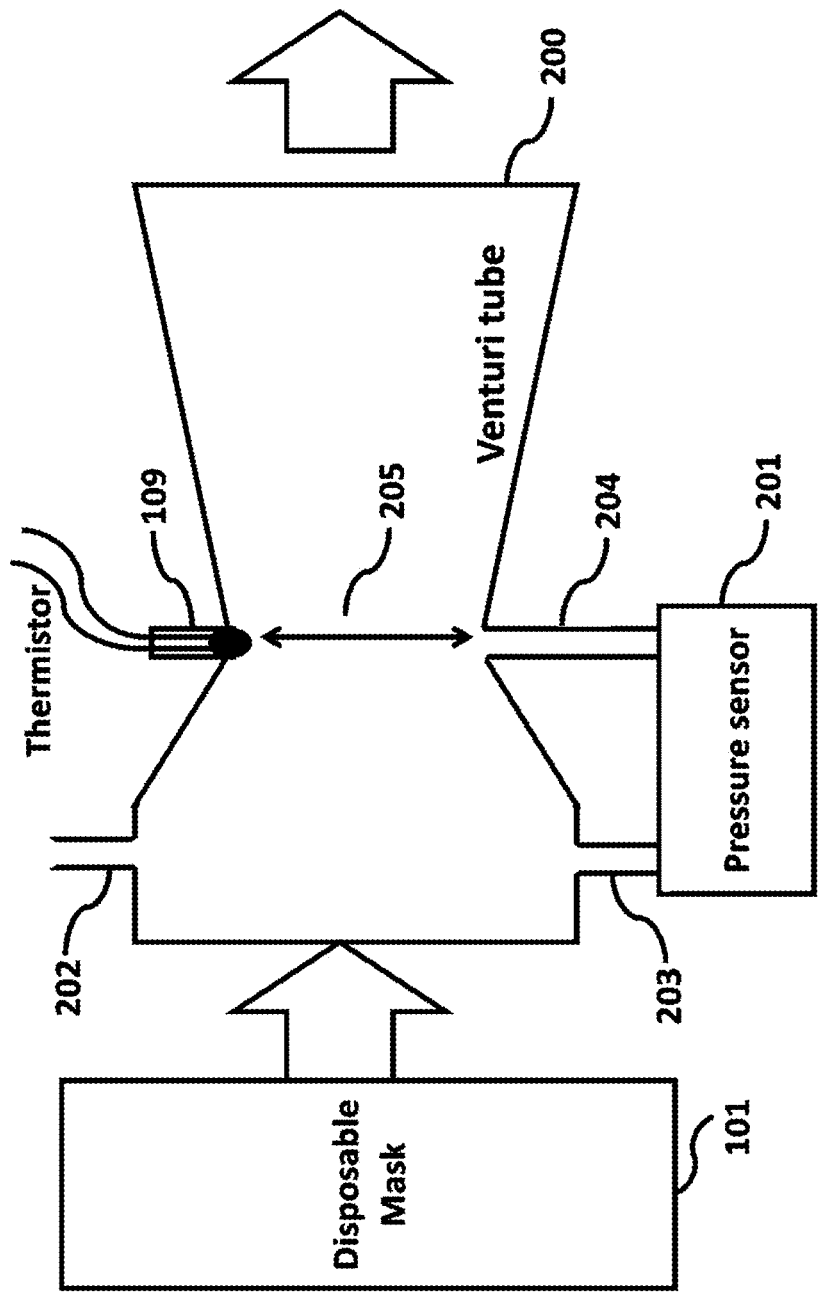
FIG. 2 illustrates an example of a flow module for a self-contained wearable metabolic analyzer.

Referring now to FIG. 2, a miniaturized Venturi tube 200 is combined with a capacitive pressure sensor 201 for breath flow rate measurement. The Venturi tube has a wide range of applications for fluid flow rate measurement, such as water meter, gasoline meter, and gas flow meter. It improves the accuracy of flow-rate measurement by building a pressure difference via creating a narrow constriction 205 with variable cross-sectional area along the flow path (channel). The relationship between differential pressure and the flow velocity is given by the Bernoulli equation, given by, $$\Delta P = \tfrac{1}{2}(pV^2), \qquad (1)$$

where $\Delta P$ is the pressure difference, p is the breath density, and V is the flow velocity at the orifices. The volume flow rate can be determined from the flow velocity at the orifice and the cross-sectional area of the narrow constriction 205.

Moreover, by designing a cone shape structure after the narrow constriction 205, the backpressure at a given flow rate is significantly decreased. Minimizing backpressure is important to help the user maintain a natural and relaxing breathing condition required for metabolic rate measurement. In other words, a large backpressure will change the user's resting condition, leading to inaccurate metabolic rate measurement. However, the detection limit of the pressure sensor must be considered while minimizing the backpressure by increasing the diameter of the narrow constriction 205 of the Venturi tube 200. If the diameter is too large, the pressure difference created by gas flow will be too small to be accurately measured by the pressure sensor. According to systematically numerical simulations and experiments carried out by the inventors herein, the diameter may advantageously be in the range of about 3-25 mm for resting metabolic rate measurements for most users. To accommodate different applications, e.g., measuring a person's metabolic rate during a physical activity or testing an infant's and child's resting metabolic rate, Venturi Tubes with different diameters of the narrow constriction 205 can be used as replaceable components. For example, by designing Venturi Tubes with various sizes, as, for example, small, medium, and large, a wide flow rate range can be covered. In other embodiments, the Venturi Tube 200 could also be replaced by other alternative mechanical designs to generate the differential pressure along the stream, such as screen and orifice.

One opening of the pressure sensor 201 is connected to the upstream of the flow path 203 in the Venturi tube 200, and the other opening of the pressure sensor 201 is connected to the downstream of the flow path 204 in the Venturi tube 200. Disposable mask 101 is connected to the upstream 203 so that the flow rate of the exhaled breath can be measured when the gas flows through the Venturi tube 200. After passing through the Venturi tube, the breath is directly vented to the ambient air. There is another opening 202 at the upstream of the Venturi tube 200. This opening 202 is designed to introduce a small portion of the entire breath to colorimetric sensing module 105 for analysis of the $O_2$ and $CO_2$ concentrations in the user's breath.

To convert the measured breath flow rate into STP flow rate for VE and REE calculation, a thermistor 109 is mounted in a pinhole at the narrow constriction of the Venturi tube 200 to monitor the breath temperature. Thermistor 109 is also used to monitor the ambient temperature before starting the metabolic measurement.

The colorimetric sensing module 105 monitors the $O_2$ and $CO_2$ concentrations of the exhaled breath. The $O_2$ and $CO_2$ concentrations, together with VE, are used to calculate the $VO_2$ and $VCO_2$ according to $$VO_2 = VE \times (0.2093 - FO_2), \qquad (2)$$

$$VCO_2 = VE \times (FCO_2 - 0.0003), \qquad (3)$$

where 0.2093 is the fraction of inspired $O_2$, $FO_2$ is the fraction of $O_2$ in the exhaled breath, $FCO_2$ is the fraction of $CO_2$ in the exhaled breath; and 0.0003 is the fraction of inspired $CO_2$, respectively.

From $VO_2$ and $VCO_2$, REE is determined by the Weir equation, $$REE\ (kcal/day) = 1.44 \times [3.9 \times VO_2 + 1.1 \times VCO_2], \qquad (4)$$

where REE represents the 24-hour energy expenditure under resting condition and the unit is kcal/day; the oxygen consumption rate $VO_2$ and carbon dioxide production rate $VCO_2$ are in the unit of mL/min.

The respiratory quotient (RQ) is defined as the ratio of $VCO_2$ and $VO_2$, given by the following equation:

$$RQ = VCO_2/VO_2, \qquad (5)$$

RQ is an indicator of the energy expenditure source (fat or carbohydrates), which has a physiological range of 0.67~1.3. Depending on the energy source, RQ values are:

Fat: 0.70

Carbohydrate: 1.00

For prolonged ketosis, RQ can be equal or less than 0.70. On the other hand, for fat storage, RQ can be larger than 1.00.

Sensors and Detection of Oxygen and Carbon Dioxide:

The $O_2$ and $CO_2$ sensors are as important as the flow sensor for accurately determining REE and RQ. At least three kinds of oxygen sensors are widely used for breath $O_2$ detection: electrochemical, paramagnetic, and fluorescence quenching $O_2$ sensors. The most common is the electrochemical $O_2$ sensors based on the galvanic fuel cell, which measures $O_2$ concentration by monitoring the oxidation current of a lead electrode. The electrochemical $O_2$ sensors are a proven technology and have been widely used in metabolic carts. Despite the popularity, they are prone to temperature variation and have limited life-time (typically, six months to one year). The paramagnetic $O_2$ sensors are based on the principle that oxygen is paramagnetic, which provides high accuracy, long life-time, and fast response time, but are prone to humidity variations. The paramagnetic $O_2$ sensors are also prone to mechanical vibration, and are bulky and expensive, which are not suitable for portable or self-contained wearable metabolic analyzers. The fluorescence quenching $O_2$ sensors are based on the principle that oxygen quenches fluorescence emission from metal organic dyes. Although the fluorescence quenching $O_2$ sensors are sensitive and fast, the quenching effect of oxygen is highly sensitive to temperature. Furthermore, the high cost and limited life-time of fluorescence quenching $O_2$ sensor are additional drawbacks for using them in self-contained wearable metabolic analyzers.

For breath $CO_2$ detection, the most widely used sensing technology is the Nondispersive Infrared (NDIR) $CO_2$ sensor. This sensor detects $CO_2$ concentration by measuring the IR absorption at a specific wavelength of light. Because $CO_2$ has a strong absorbance at the wavelength of 4.26 μm, this wavelength is typically used for $CO_2$ detection. One issue with the NDIR $CO_2$ sensor is the spectral interference caused by water vapor. For this reason, humidity in breath must be conditioned or removed to achieve accurate and reproducible detection of breath $CO_2$ with this type $CO_2$ sensor.

The $O_2$ and $CO_2$ sensors are based on different signal transduction principles, and consequently are two isolated units, which are problematic to be integrated into a single unit for a wearable device. More specifically, using of the $O_2$ and $CO_2$ sensors described in the published teachings face the following challenges: 1) the size of the $O_2$ and $CO_2$ sensors is big, 2) the weight of the $O_2$ and $CO_2$ is heavy, 3) their output signals are completely different, which adds burden to signal conditioning, amplification circuit, and processing software, and 4) uniform delivery of breath sample to the two isolated sensors require complicated flow design.

As described above, prior patents and applications by some of the inventors herein, and published as US2013/0150746 A1 (allowed) and U.S. Pat. No. 10,078,074 address the above challenges by disclosing a single integrated colorimetric sensor chip, each consisting of $CO_2$ and $O_2$ sensing elements. Compared to conventional chemical sensors, the sensor chip detects multiple analytes (e.g., $CO_2$ and $O_2$) with an array of sensing probes, where each target a chemical analyte. Because both sensing elements are colorimetry based, signal readout is simple, requiring only a light source (LED) and an array of photodetectors. Despite of the success, the sensor chip is directly exposed to the full breath and integrated along the breath path flow together with a thermistor, flowmeter, and the optoelectronic detection unit, comprising a LED and photodetector array. The design is prone to effects of water condensation, temperature variability, and breath flow turbulence. All these compromise the accuracy of $CO_2$ and $O_2$ analysis, which must be corrected with sophisticated hardware, such as a special mechanism to affix the sensor into the sensing chamber to buffer turbulence from breath flow; a mechanical fan to dry out water condensation after each measurement; etc. This additional hardware brings complexity in the design, bulkiness, ambient noise (when fun is running) as well as energy consumption. On the other hand, a modular approach as disclosed here will make the design extremely easy to assemble, to calibrate, to isolate issues and to repair/replace a component.

After performing thousands of tests with devices based on the prior art by us, the inventors developed and tested new designs with innovative solutions to the above-described issues. In one example, the present disclosure features a colorimetric sensing module 105 (FIG. 3), which is an integral part of a self-contained wearable metabolic analyzer, yet it functions as a sensing unit for simultaneous analysis of $CO_2$ and $O_2$ in breath. Additional sensing elements may be included on the sensor chip for detection of other chemical analytes. The detection module uses common consumer electronic components, such as LED and photodiodes, and the sensor chip is made from common chemicals and plastics fabricated with printing and plastic molding methods. The sensor module consists of a miniaturized detector chamber into which a sensor chip is inserted. The detector chamber has an inlet and an outlet, for guiding a small fraction of breath from Venturi tube assemble 200 via the opening 202 at the upper stream of 200 without using a mechanical pump or fan.

Figure 3A:
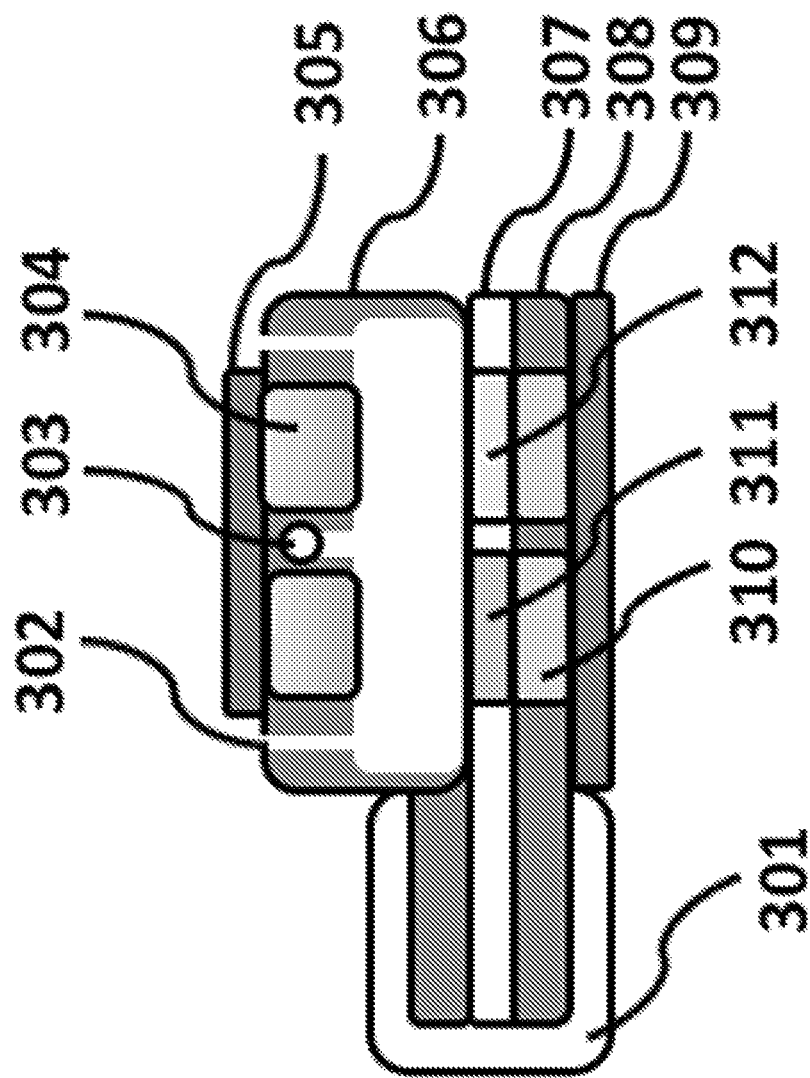
FIG. 3 illustrates the side view (a), top view (b), and simulated flow distribution of an example of a colorimetric sensing module.
Figure 3B:
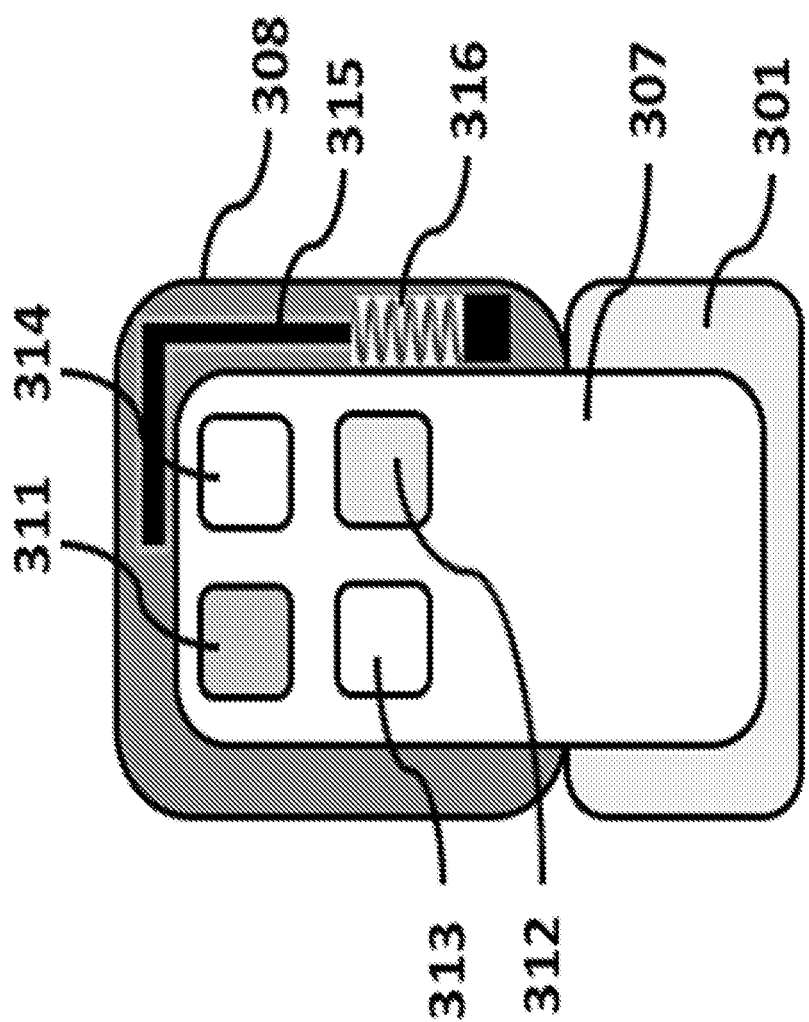
Figure 3C:
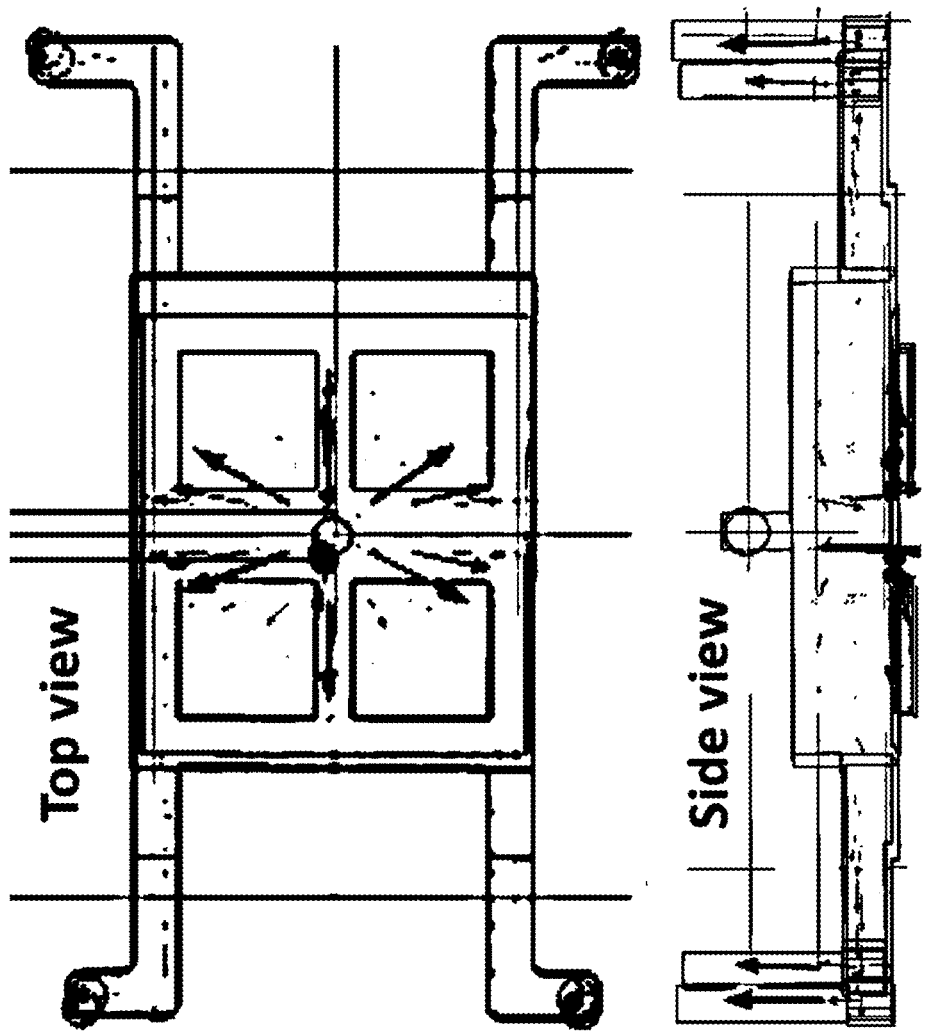

Referring now to FIGS. 3A and 3B, an example of schematics showing a side view and a top view of a colorimetric sensing module 105 is shown. The colorimetric sensing module has a plurality of components including LED array 304 and circuit 305, top support piece 306, photodiode 310 and circuit 309, bottom support piece 308, chamber cover 301, and sensor chip 307. LED array 304 provides uniform illumination to the sensor chip 307. In one embodiment, one LED for each of the four sensing areas, including $CO_2$ sensing area 311, $O_2$ sensing area 312, $CO_2$ reference area 313, and $O_2$ reference area 314, making a total number of 4 LEDs. Because the color changes for $O_2$ and $CO_2$ reactions on the sensing areas are more sensitive to red light, in this embodiment, the LEDs with illuminating wavelength of 630 nm are used, and therefore the measurement of both gases is made at a single absorption wavelength. LED circuit 305 is assembled onto the top support piece 306 (FIG. 3a). Inlet 303 is a breath (gas) channel with a diameter of ~1 mm, starting from one side of the top support piece 306, and ending near the center of the top support piece 306, making a 90-degree turn downward to guide breath to flow uniformly across all the four sensing areas of the sensor chip 307. At the four corners of the top piece 306, there are four outlets 302, allowing breath to vent without causing substantial water condensation.

The colorimetric sensing module 105 is designed so that 1) there is gap of 1-3 mm formed between the bottom surface of the top supporting piece 306 and the top surface of the sensor chip 307; and 2) one breath inlet is located in the center of the top supporting piece 306 and four outlets are symmetrically located at the four corners. As shown in the simulated flow distribution in FIG. 3C, this geometry allows sufficient mix and symmetric flow distribution of the breath sample inside the colorimetric sensing module 105 and effective reaction between the chemical analytes and the sensing probes in each sensing areas of the sensor chip 307. In addition, this module design avoids turbulent flow, which can speed up the sensor reaction and preclude the life-time of the sensor from sensing at longer times (e.g. 10 min.).

A photodetector assembly, includes photodiode circuit 309 and photodiodes array 310. In this embodiment, at least four photodiodes, one for each sensing area, are used. The four LEDs 304, sensing areas, and the photodiodes 310 are aligned in the colorimetric sensing module 105. Photodiode circuit 309 is mounted onto the bottom piece 308 that has a sensor chip "lock-in" and "pop-up" mechanism, achieved using a L-shape holder 315 and a spring 316, as shown in FIG. 3B.

The sensor chip 307 is a plastic-molded substrate made from inert polymers, and coated with $O_2$ and $CO_2$ sensing probes. There are four sensing areas on the sensor chip 307: $CO_2$ sensing area 311, $O_2$ sensing area 312, $CO_2$ reference area 313, and $O_2$ reference area 314. The $CO_2$ sensing area 311 and $O_2$ sensing area 312 are uniformly coated with certain amount of $CO_2$ and $O_2$ sensing probes, respectively, which specifically react with $CO_2$ and $O_2$ in breath. $CO_2$ reference area 313 and $O_2$ reference area 314 are used for correcting the optical signal drift during the measurement due to the light intensity variation and non-chemical reactions. Chamber cover 301 is a cover made from rubber plastic. Once the sensor chip 307 is inserted into the colorimetric sensing module 105, chamber cover 301 is used to provide an air-tight sealing of the colorimetric sensing module 105. The chamber cover 301 should be non-transparent so that it can block the ambient light to avoid any optical interference to the colorimetric detection.

Mixing chamber technology is a widely used method for metabolic rate measurement, where the exhaled breath is introduced to a mixing chamber through a non-rebreathing (one-way) valve for uniform mixing to avoid the short-term fluctuation of the analyte concentration. However, typically, a mixing chamber has a large volume (4-6 L), which is not suitable for a wearable device. The present disclosure introduces inhalation and exhalation one-way valves directly on the disposable mask 101 to ensure non-rebreathing for the exhaled breath. It also uses only a small portion, less than 1%, of the entire breath delivered to the colorimetric sensing module 105, where the breath sample is mixed and then reacts with the sensing probes for $CO_2$ and $O_2$ analysis. This is possible because the structure disclosed here ensures that the volume of breath delivered to the colorimetric sensing module 105 is proportional to the volume of breath exhaled through the Venturi tube. To achieve an effective gas mixing in colorimetric sensing module 105, simulation has been performed to evaluate the flow distribution, pressure, turbulence, flow dynamics, and mass transportation for chemical reaction on different geometries and dimensions.

Figure 16:
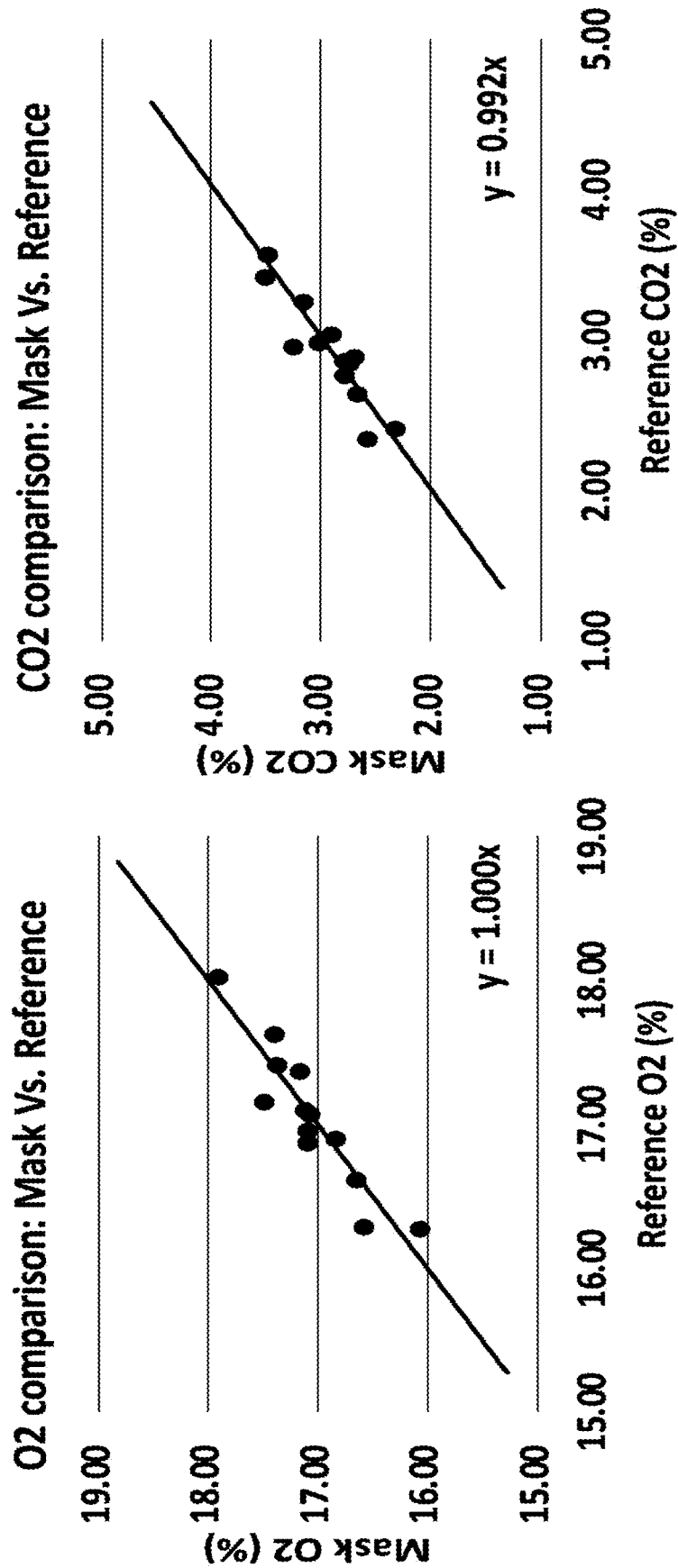
FIG. 16 shows an example of correlation of breath $O_2$ and $CO_2$ concentrations measured by a colorimetric chemical sensor included in a self-contained wearable metabolic analyzer and reference methods.

Now referring to FIGS. 6A and 6B, illustrations of an example of an optimized design and its performance that has been verified by both the simulation results in FIG. 6C and the accuracy of measured $O_2$ and $CO_2$ concentrations presented in FIG. 16 are shown. A calibration mechanism is invented to directly relate the flow rate measured by the flow module 104 with the flow rate into the detection colorimetric sensing module 105. The calibration mechanism uses that the color development on the sensing area dependence on analyte concentration and mass transportation.

Figure 4A:
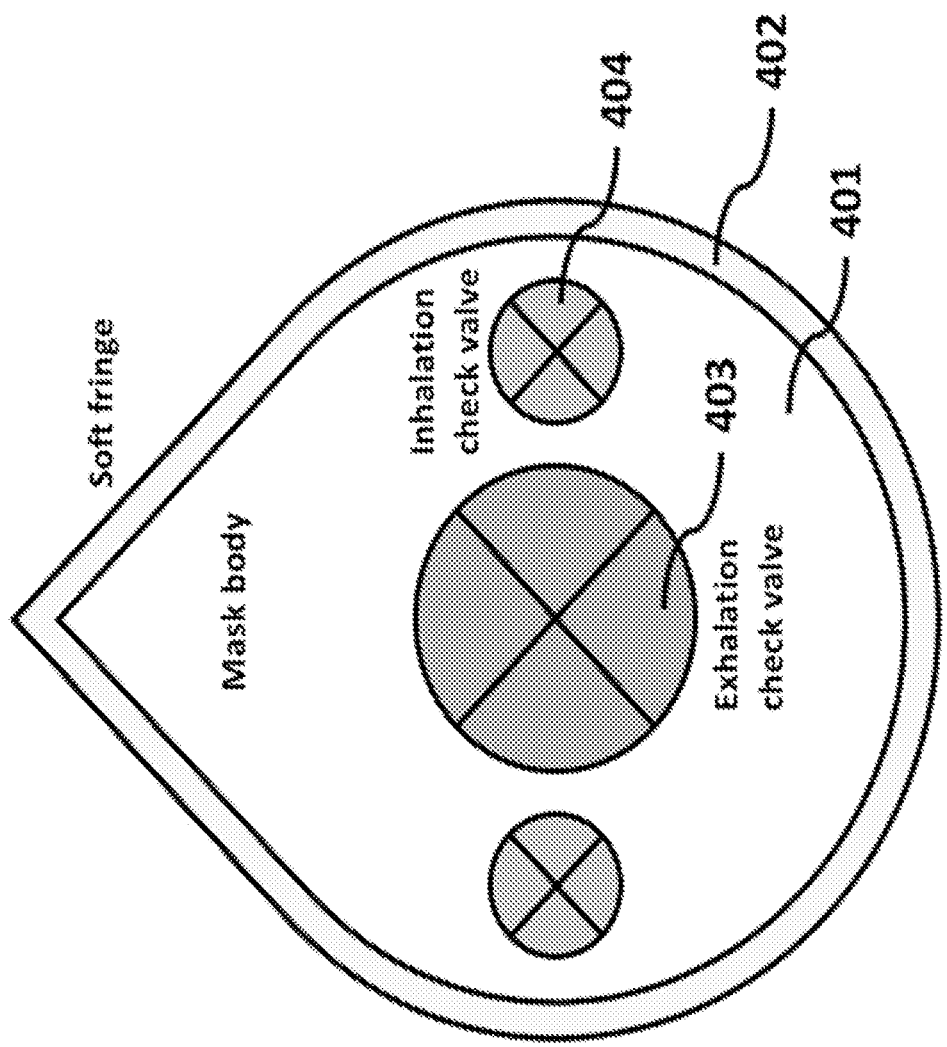
FIG. 4 illustrates the front view (a) and side view (b) of an example of a disposable mask.
Figure 4B:
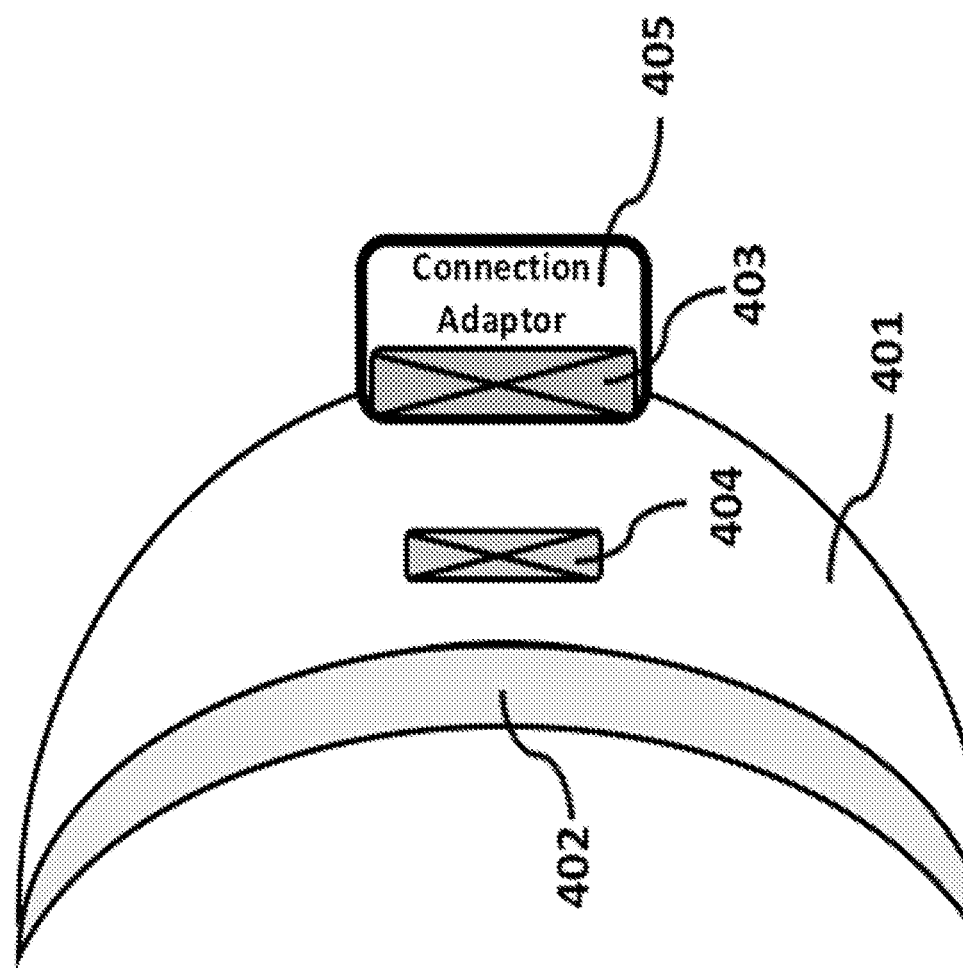

Metabolic Analyzer Design, Parts, Assembly and Wearability:

Now referring to FIGS. 4A and 4B, schematics illustrating examples of a front view and side view of the disposable mask 101 are shown. The disposable mask has at least five major components including mask body 401 with a soft cushion 402 along the edge, exhalation one-way valve 403, inhalation one-way valves 404, and connection adaptor 405. Mask body 401 is a plastic-molded piece with concave shape that fits the profile of human face. Soft cushion 402 is made from a soft material to provide comfortable and air-tight sealing with the face during the measurement. Exhalation valve 403 is a non-rebreathing (one-way) valve located in the middle of mask body 401, which allows the exhaled breath flow freely out of the disposable mask 101 to reach the Venturi tube 202. In order to minimize the exhalation flow resistance, the diameter of the exhalation one-way valve 403 should be in the range of 20~40 mm. For inhalation, inhalation one-way valves 404 are used to allow fresh ambient air to be inhaled into the mask by the user. Multiple inhalation one-way valves 404 can be implemented to minimize inhalation flow resistance. Connection adaptor 405 is a part of the disposable mask 101 to provide air-tight connection to the Venturi tube 202 when the disposable mask 101 is assembled with the device body 100. For users with different face shapes and sizes, disposable masks of different sizes, such as small, medium, and large sizes, are preferred. The disposable mask 101 can be detached from the device body 100 for disinfection. Because of the non-rebreathing feature of the disposable mask 101, cross-contamination of different users is avoided.

Figure 5:
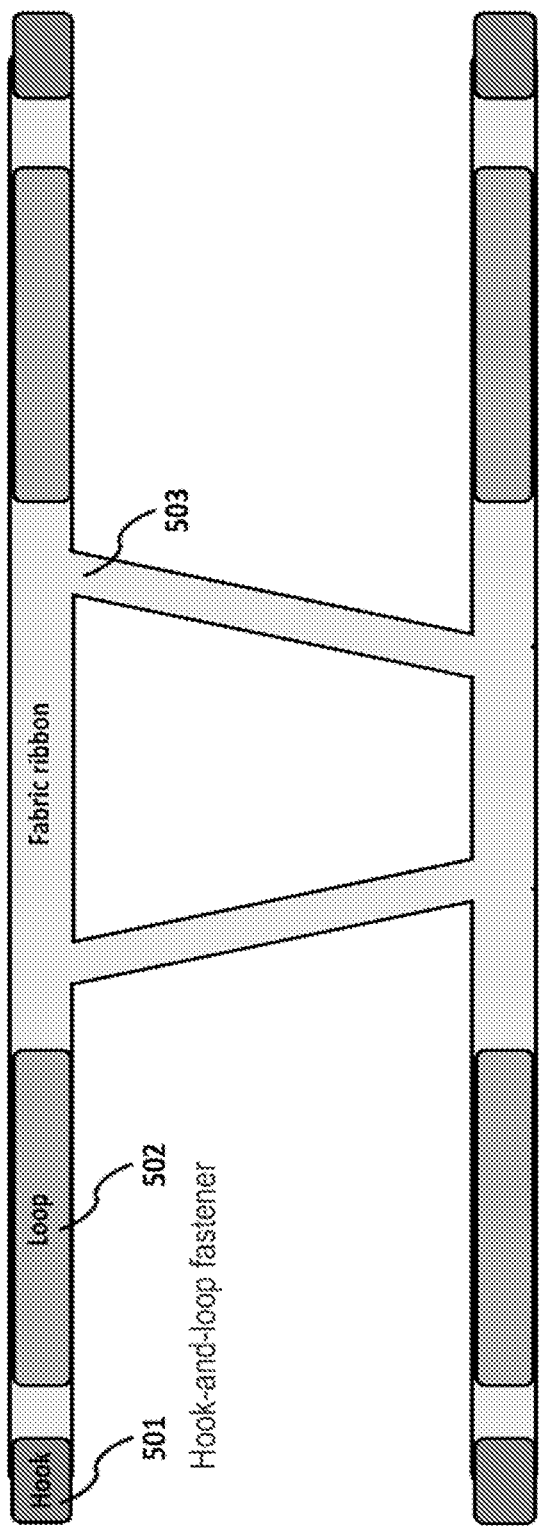
FIG. 5 illustrates the structure of an example of headgear for a self-contained wearable metabolic analyzer.

Now referring to FIG. 5, a schematic illustrating an example of headgear 102 for fastening the disposable mask 101 with the device body 100 is shown. The headgear includes fabric ribbons 503 for wrapping around the user's head. In order to have a balanced and stable positioning of the device body, in one embodiment double strips are used and four contacting points are made with the device body. In one embodiment, a hook(501)-and-loop(502) fastener is used to provide an easy and adjustable way for the user to wear.

Figure 6:
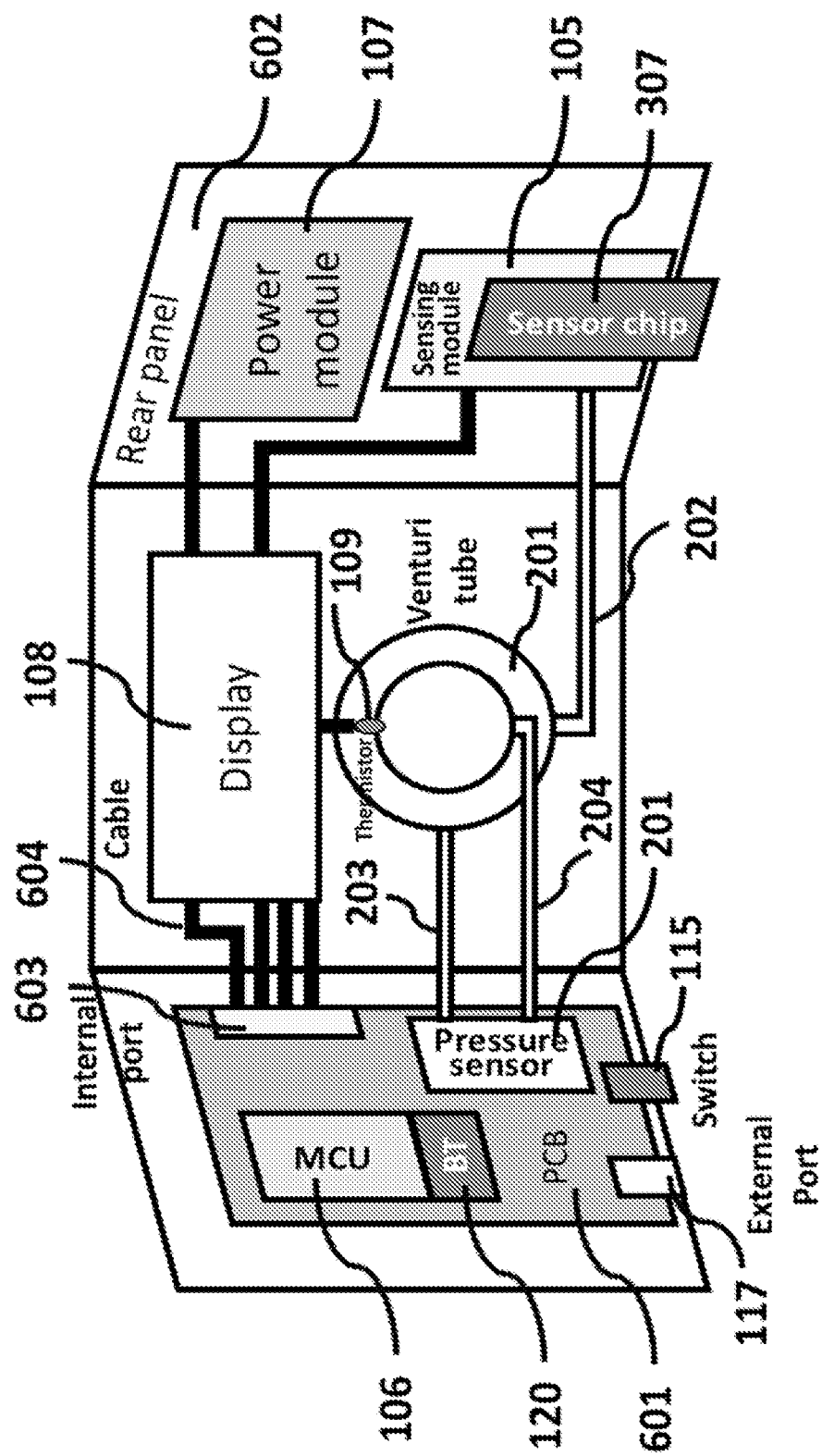
FIG. 6 illustrates of a front view of an example of an assembled device body of a self-contained wearable metabolic analyzer.

Now referring to FIG. 6, a schematic illustrating an example of a front view of one embodiment of the device body 100. The device body 100 is arc-shaped, matching the shape of human face. The device body 100 includes left, middle, and right sections. The mechanical and electrical components are distributed in different sections according to their functions and considering weight balance within the device. All the components are fixed on the rear panel 602 of the device by fastening elements such as, for example screws or the like.

The left section is assembled with a printed circuit board assembly (PCBA) 601. A microcontroller unit (MCU) 106 controls other electronic components and processes signals from different sensors. In one example, a transmission module 120 such as, for example a Bluetooth® (BT) module or an equivalent, is responsible for data communication between the device body 100 and the tablet/phone/computer 103. Pressure sensor 201 is located on the PCBA 601 with two openings connected to the upstream 203 and downstream 204 of the Venturi tube 200. Switch 115 is located on the bottom of the PCBA 601 with its push button standing out for operation. Electrical connector 603 connects other separate electronic components, including power module 107, display module 108, and thermistor 109, via cables 604. Breath temperature reading from the thermistor 109 is used to convert the volume flow rate of breath into the standard temperature and pressure (STP) condition. Signal port 604 is a mini USB port in this embodiment, which can be used for both data communication and battery charging. Other electronic components on the PCBA 601 (also refer to FIG. 1 for more details) include:

1) Humidity sensor 110 for monitoring the ambient humidity level. If the ambient humidity level is higher than the allowed operation humidity level. In one example, an alert message will be displayed to remind the user to comply with the operation condition.

2) Barometer 111 monitors the ambient barometric pressure. Data from the barometer may be used to warn the user if the ambient barometric pressure is out of the range of the allowed operation level. The barometric pressure reading is also used to convert the volume flow rate of breath into the standard temperature and pressure (STP) condition.

3) Buzzer 113 provides sonic feedback to the user during the measurement when certain action is performed, such as device is turned on/off; or the measurement is finished.

4) Gyroscope 114 is mounted to detect the orientation of the device body during the measurement. This information is used to correct the orientation-induced baseline change of the pressure sensor. The gyroscope may be replaced by an accelerometer or other sensors to determine the orientation of the device.

5) Reset 116 allows the user to reset the device to default conditions when desired as a fail-safe feature.

6) Memory 118 is used for storing firmware code and test data.

7) Clock chip 119 is used for creating a time stamp for the measurement. To allow the clock chip running continuously for a very long time (e.g. 5-10 years), a coin battery with large power capacity is dedicated to drive the clock chip, even when the device body is switched off.

8) LED indicators 112 provide visual feedback to the user about the status of the device, such as battery power level, charging status, the measurement status.

The middle section is assembled with display module 108, Venturi tube 200, and thermistor 109. In this embodiment, the display module 108 is an OLED display, which can show the text, numbers, and graphics. Other displays, such as LCD display, segment displays, and touch screen display may be used in other embodiments. The display can show different information to the user during the measurement, including but not limited to 1) the status of a self-contained wearable metabolic analyzer (ready, measuring in progress, finished); 2) the battery level; 3) the charging status; 4) the Bluetooth® connection status; 5) the test result; 6) the alert; 7) the operation instruction; 8) other message related to the measurement.

The right section is assembled with power module 107 and the colorimetric sensing module 105. The power module 107 consists of a battery and charging circuit. The opening of the colorimetric sensing module 105 is aligned with the slot on the housing for pushing in and popping out the sensor chip 307. The breath inlet of colorimetric sensing module 105 is connected with the opening 202 on the Venturi tube 200

Figure 7:
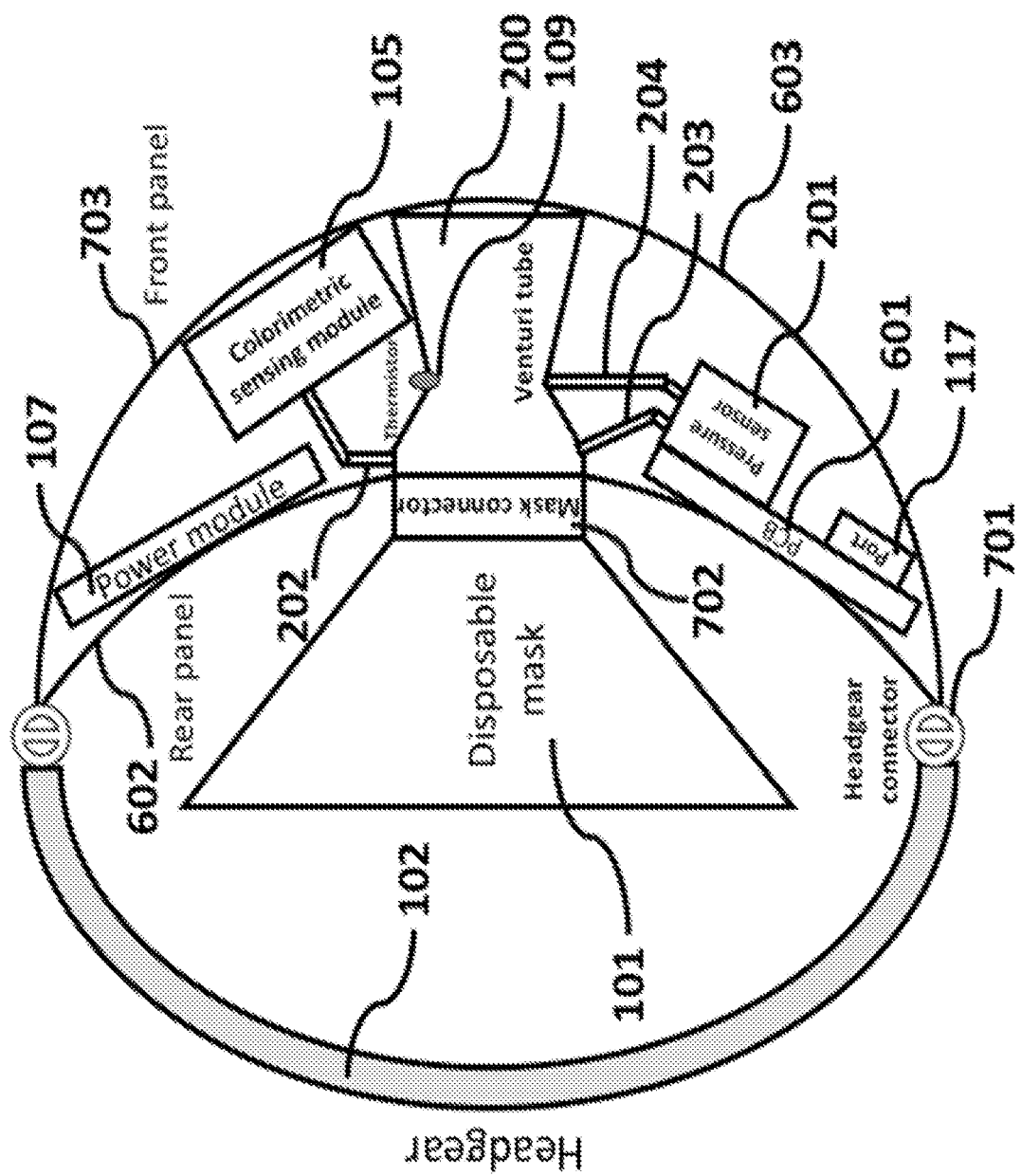
FIG. 7 illustrates of a top view of an example of an assembled device body with disposable mask and headgear.

Referring now to FIG. 7, an example of a schematic illustrating the top view of one embodiment of the assembled device body 100 with disposable mask 101 and headgear 102 is shown. The headgear 102 is attached to the headgear connectors 701 on both sides of the device body 100, and the disposable mask 101 is assembled to the device body 100 through the mask connector 702. The front panel 703 and the rear panel 602 of the device body 100 are assembled together to form an enclosed housing. The front panel 703 is designed with the corresponding windows and openings for the display 108, LED indicators 112, switch 115, reset 116, and external port 117. The logo, model name, and symbols of the product can also be screen printed on the front panel 703. To control the weight of the device body 100, the front panel 703 and the rear panel 602 are made from plastic materials.

Figure 8B:
FIG. 8 schematically illustrates an example of a sensor chip and QR code.
Figure 8A:
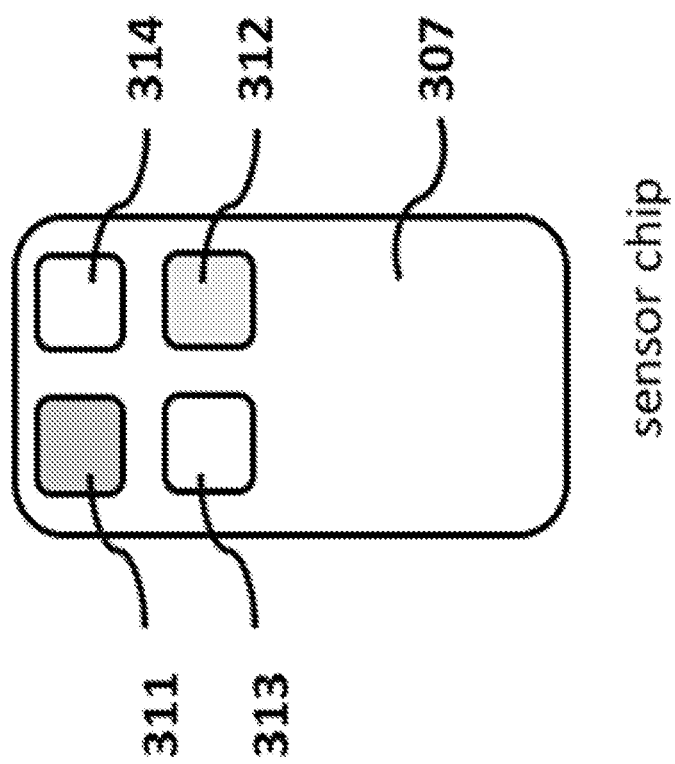

Referring now to FIG. 8A, an example of a schematic illustrating one embodiment of the sensor chip 307 is shown. The sensing areas are engraved with micro features, which is the key for uniformly dispersing the solutions of sensing probes on the sensing areas to avoid the "coffee-ring" effect. The information of each sensor chip is encoded into a QR code, as shown in FIG. 8b, which is read by the phone/tablet/computer 103 and transmitted to the device body 100 via Bluetooth® 120.

Figure 9:
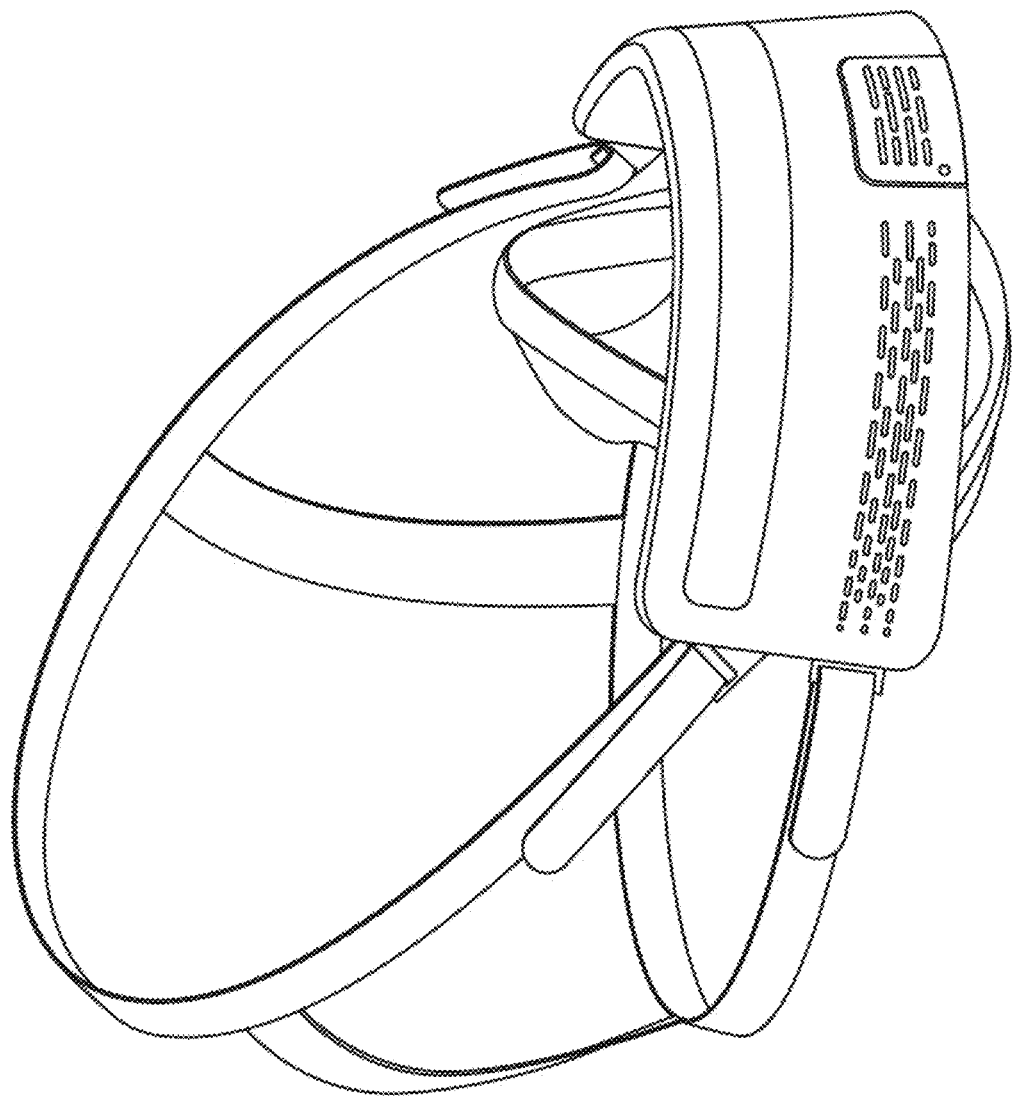
FIG. 9 illustrates an example of a self-contained wearable metabolic analyzer.

Referring now to FIG. 9, an example of a schematic illustrating one embodiment of the wearable, integrated, and stand-alone device body 100 assembled with disposable mask 101 and headgear 102 is shown.

Figure 10:
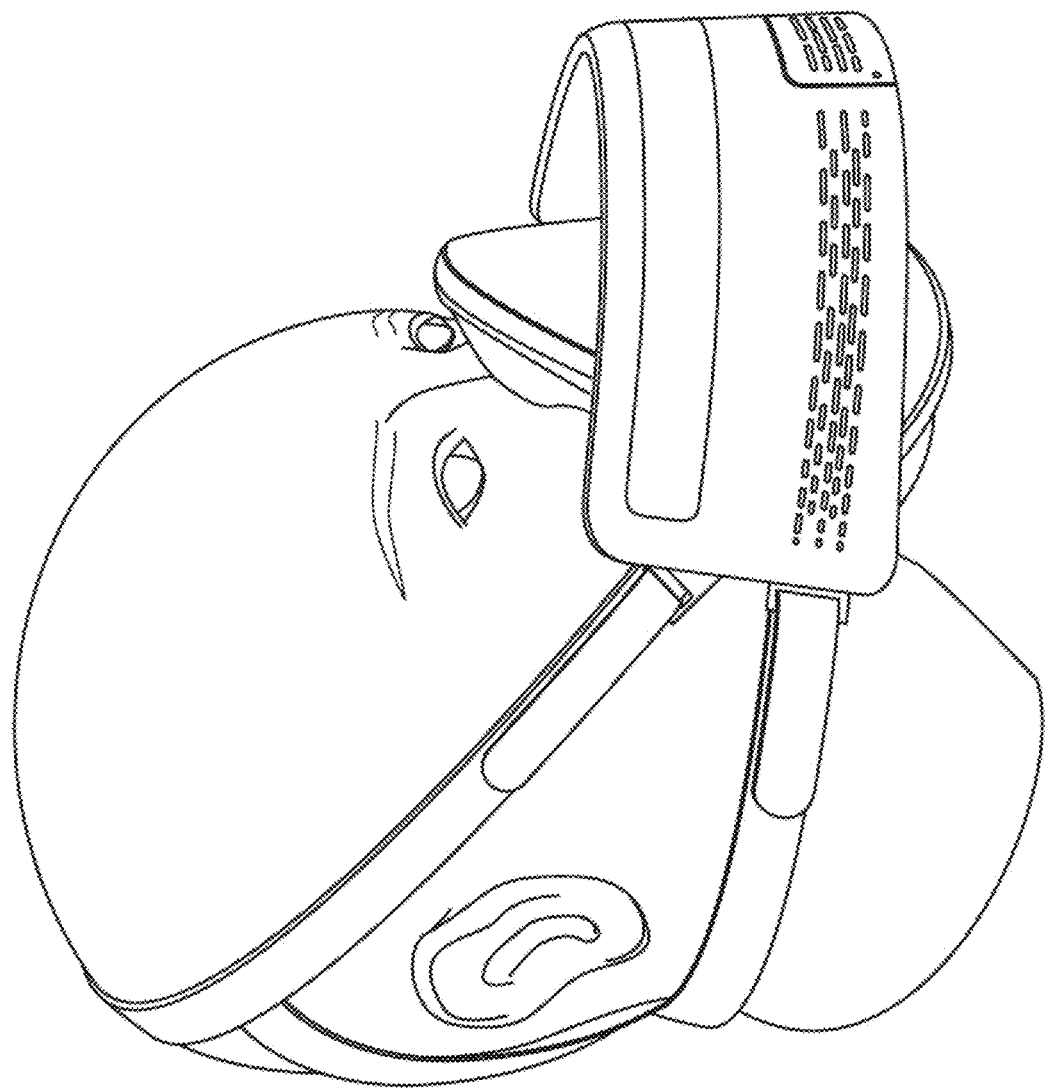
FIG. 10 illustrates an example of use of a self-contained wearable metabolic analyzer for REE and RQ measurements.

Referring now to FIG. 10, an example of a schematic illustrating the using of the fully assembled self-contained wearable metabolic analyzer on a user's head for metabolic rate measurement is shown. Device body 100 is compact, disposable mask 101 covers the nose and mouth of the user, and the headgear 102 wraps around the head of the user and holds the entire self-contained wearable metabolic analyzer tight and stable on the face.

Figure 11:
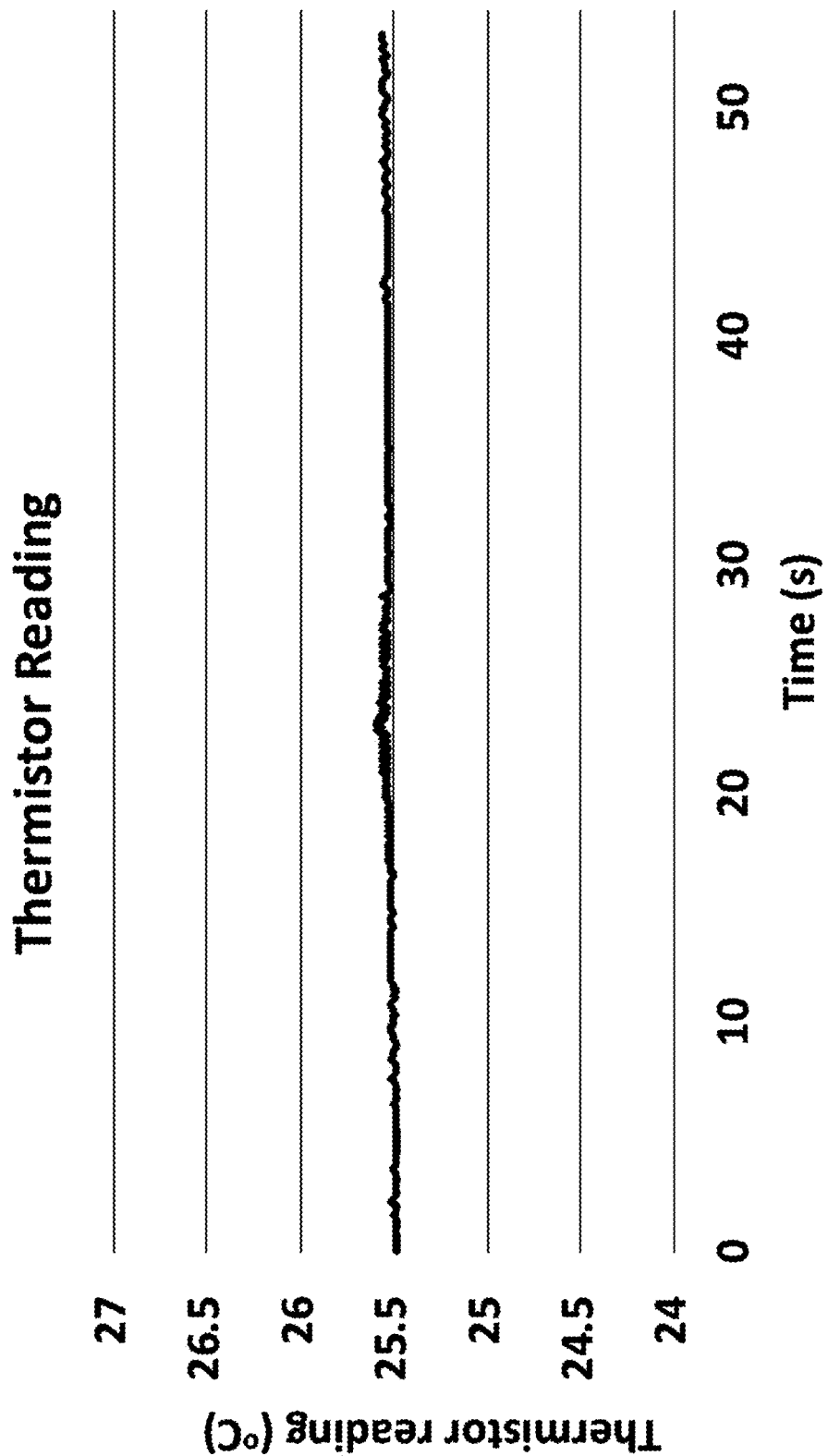
FIG. 11 shows example of a temperature reading from the thermistor of a self-contained wearable metabolic analyzer for environmental temperature monitoring.
Figure 12:
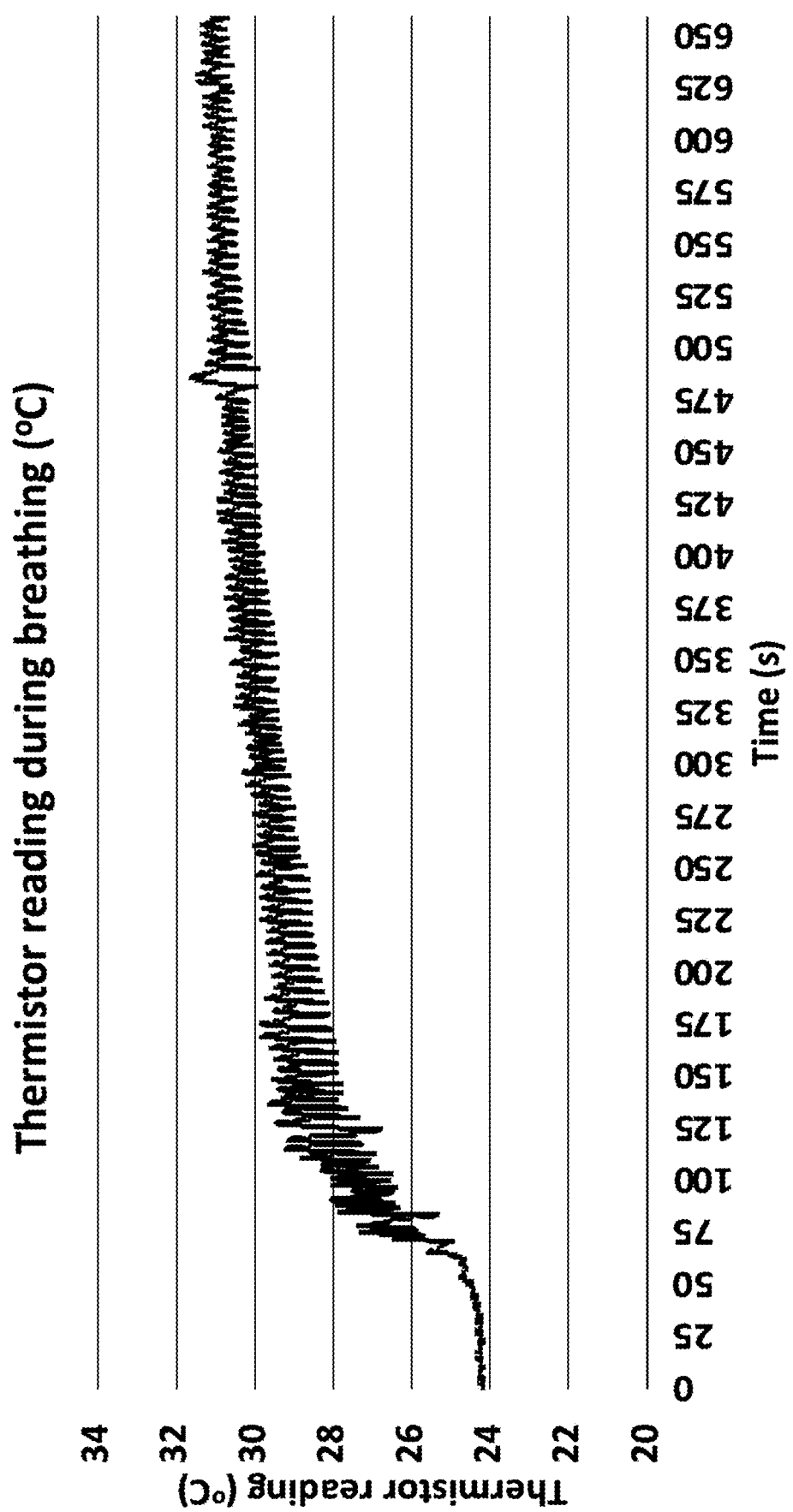
FIG. 12 shows an example of a temperature reading from a thermistor used in a self-contained wearable metabolic analyzer for breath temperature monitoring.

Self-Contained Wearable Metabolic Analyzer's Sensor Performance:

Referring now to FIG. 11, an example of a temperature reading from the thermistor 109 of the device body 100 for environmental temperature monitoring shown.

Figure 13:
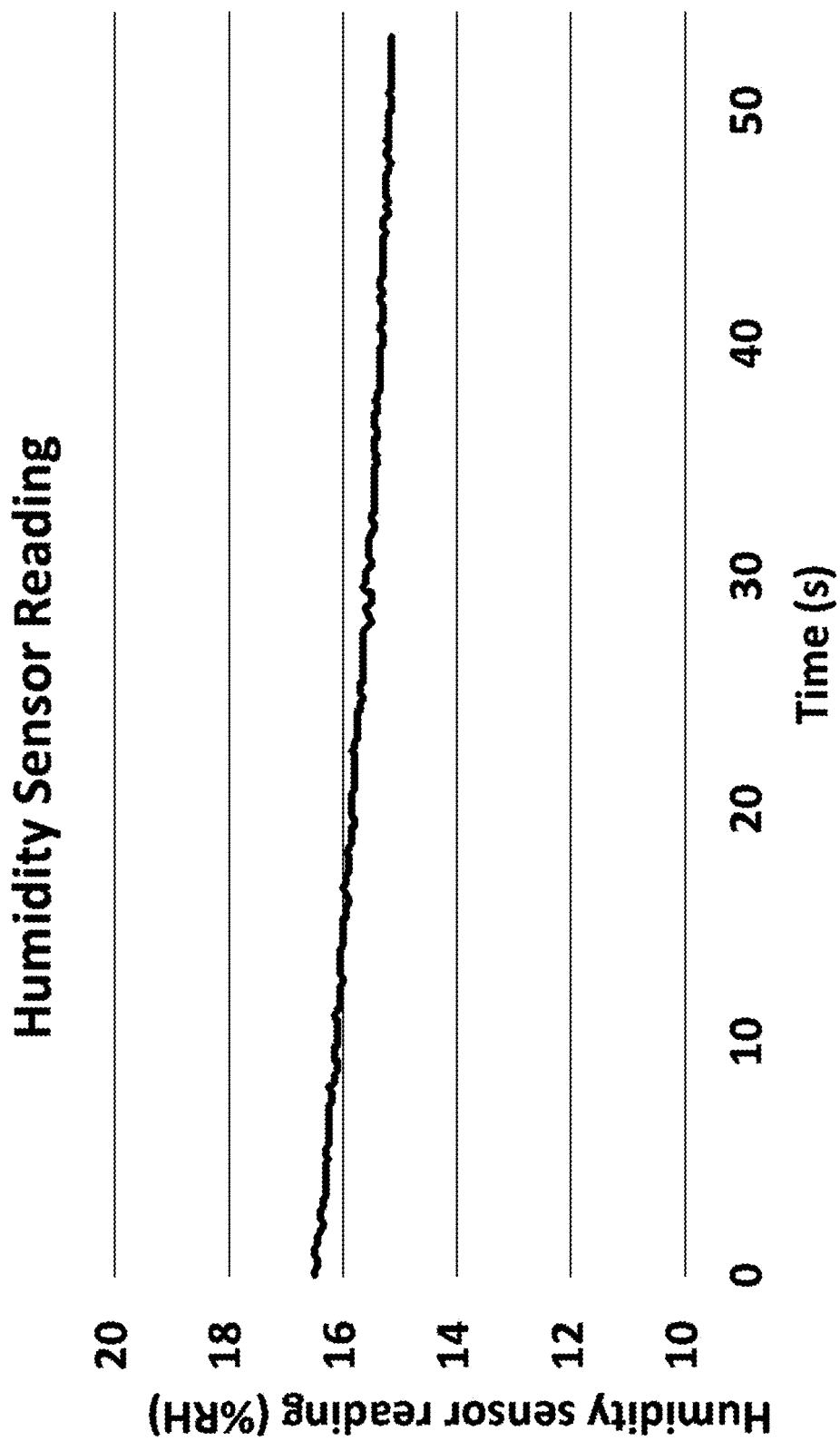
FIG. 13 shows an example of a humidity reading from a humidity sensor used in a self-contained wearable metabolic analyzer for environmental humidity level monitoring.

Referring now to FIG. 13, an example of a humidity reading from the humidity sensor 110 of the device body 100 for environmental humidity level monitoring is shown.

Figure 14:
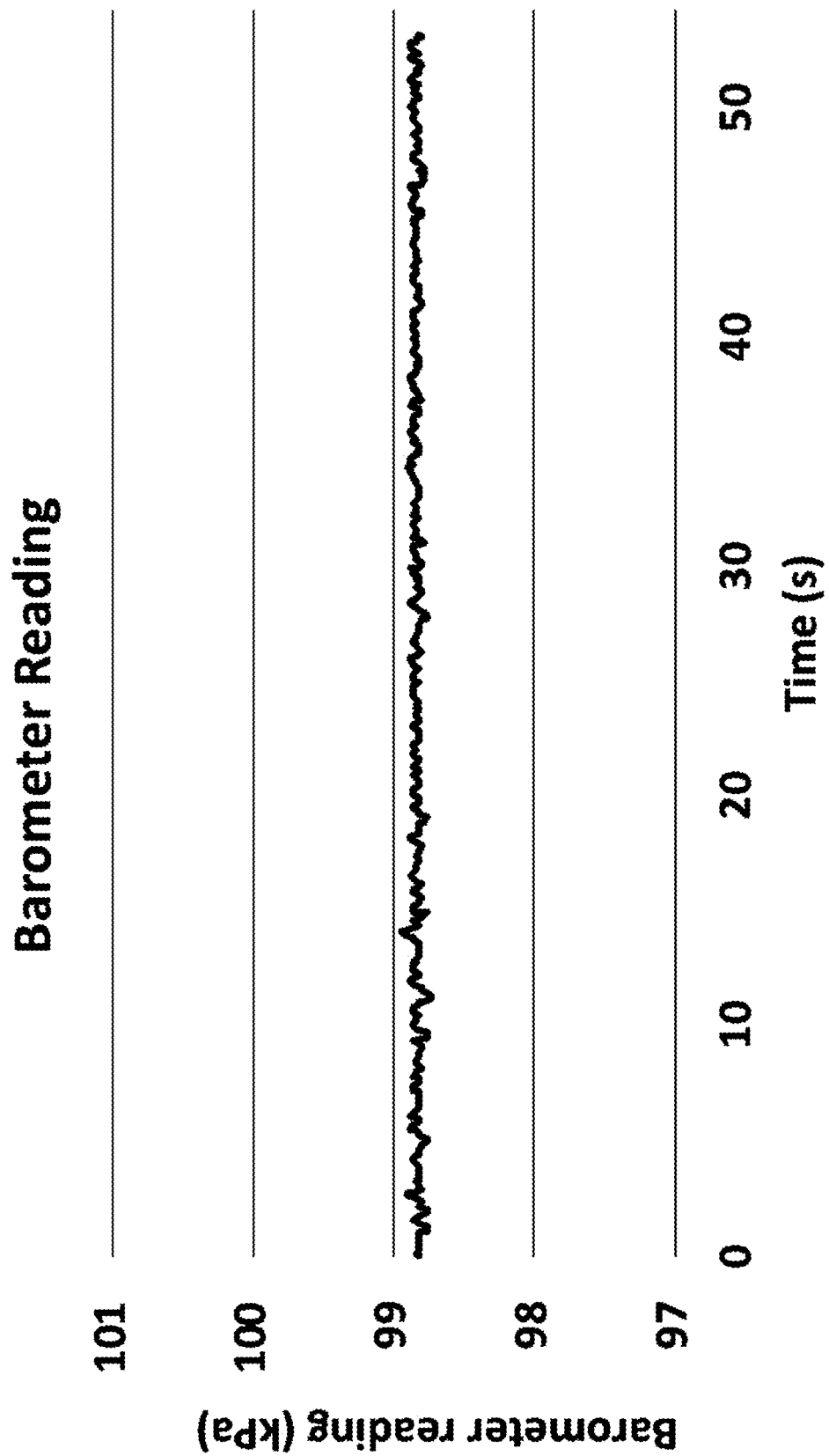
FIG. 14 shows example of a barometric pressure reading from a barometer used in a self-contained wearable metabolic analyzer for environmental barometric pressure monitoring.

Referring now to FIG. 14, an example of a barometric pressure reading from the barometer 111 of the device body 100 for environmental barometric pressure monitoring shown.

Figure 15:
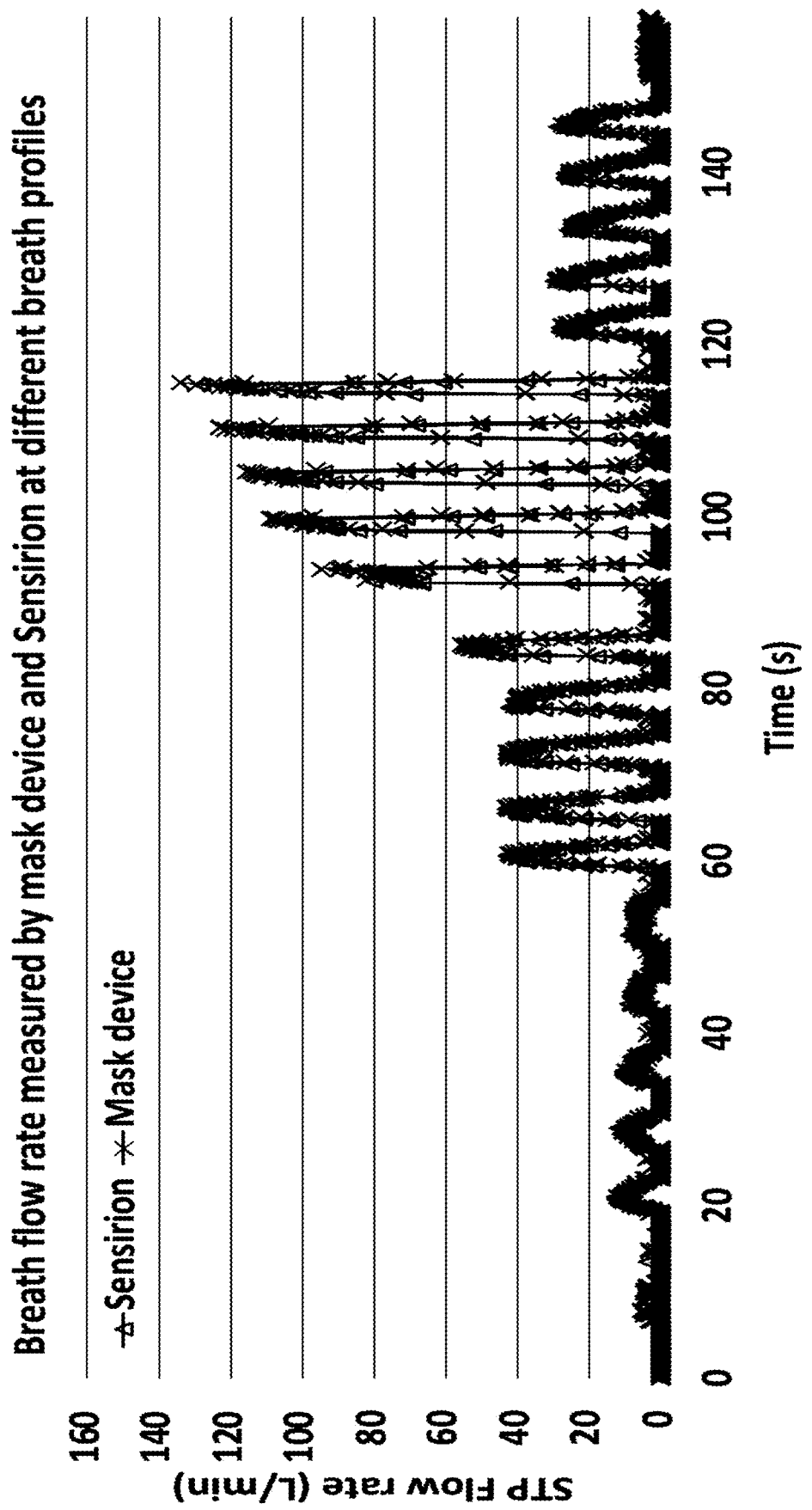
FIG. 15 shows an example of correlation of breath flow rate measured by a self-contained wearable metabolic analyzer and a reference method of different breath profiles.

Referring now to FIG. 15, an example of correlation of breath flow rate measured by the flow module 104 of the device body 100 and reference flow meter (Sensirion) at different breath profiles is shown.

Referring now to FIG. 16, an example of correlation of breath $O_2$ and $CO_2$ concentrations measured by colorimetric sensing module 105 on the device body 100 with reference methods is shown.

Figure 17:
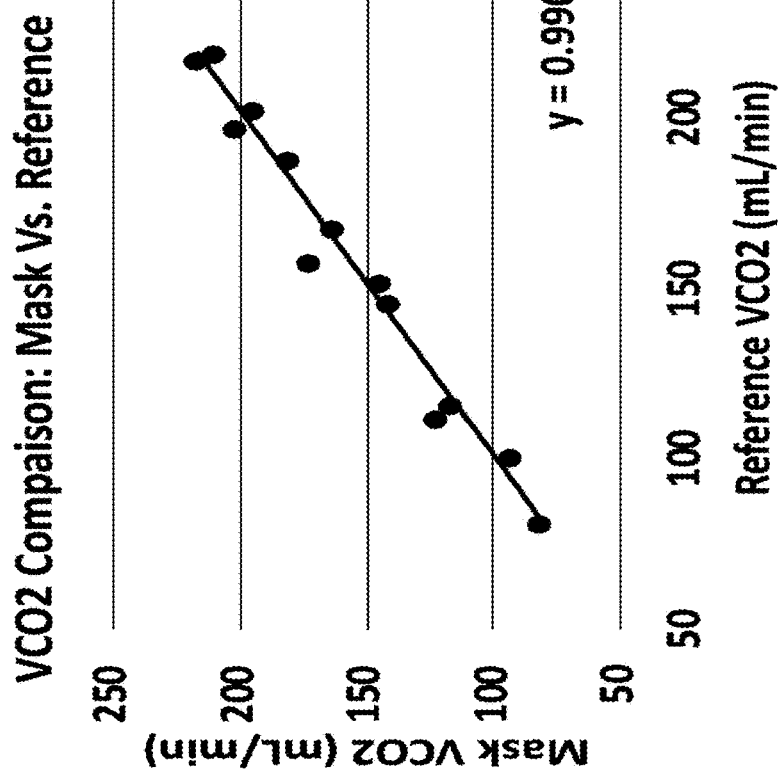
FIG. 17 shows the correlation of $VO_2$ and $VCO_2$ measured by the self-contained wearable metabolic analyzer and reference method.
Figure 17:
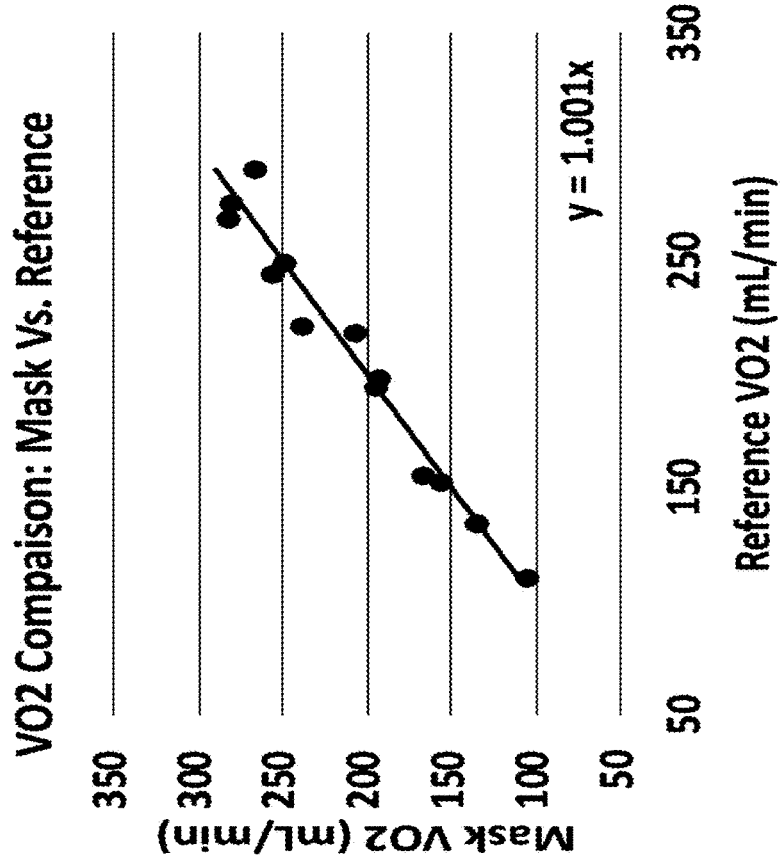

Referring now to FIG. 17, an example of correlation of $VO_2$ and $VCO_2$ measured by the device body 100 and reference method is shown. The $VO_2$ and $VCO_2$ were calculated according to equations (2) and (3) based on the readings from the flow module 104 and colorimetric sensing module 105.

Figure 18:
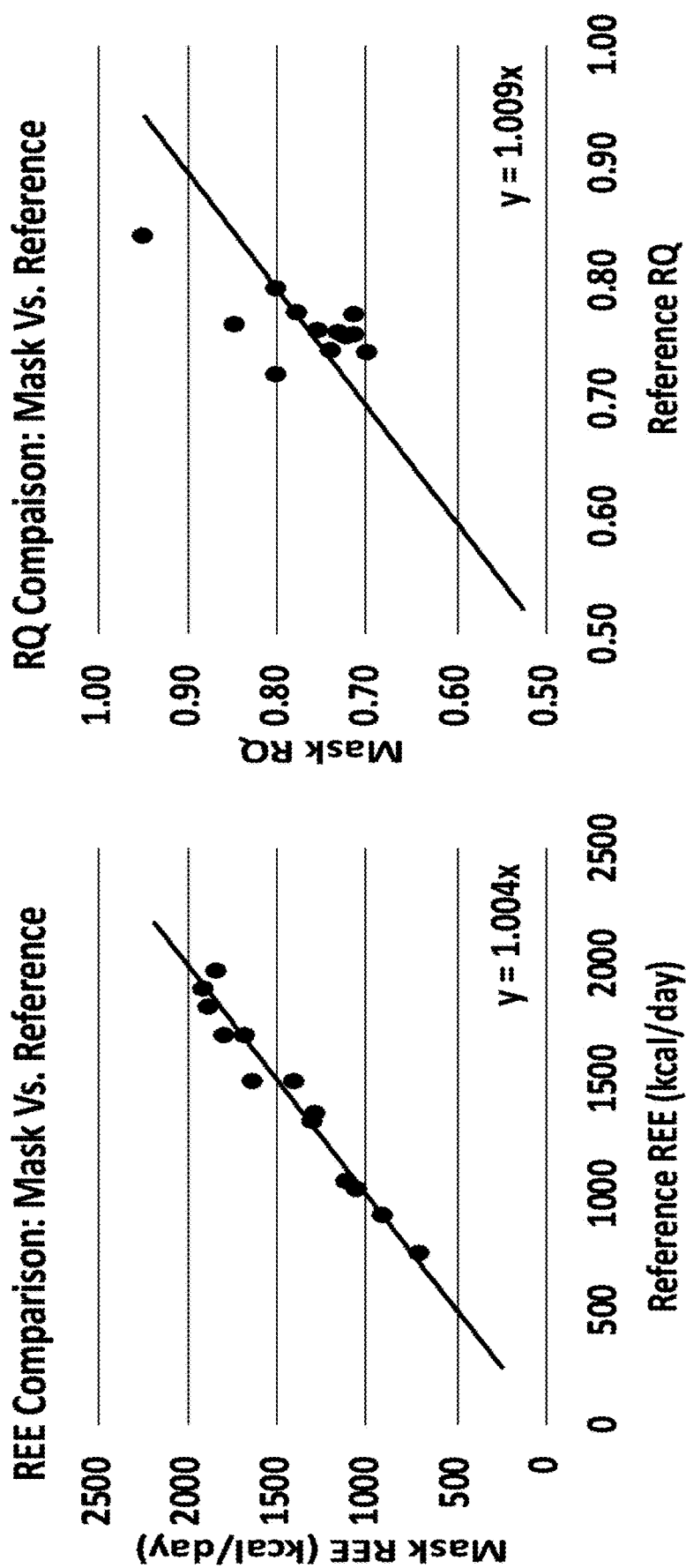
FIG. 18 shows an example of correlation of REE and RQ measured by a self-contained wearable metabolic analyzer and reference method.

Referring now to FIG. 18, an example of correlation of REE and RQ measured by the device body 100 and reference method is shown. The REE was calculated according to equation (4) and RQ was calculated according to equation (5).

The results shown above substantially demonstrate performance of a self-contained wearable metabolic analyzer's sensors (FIGS. 11-15), and the accuracy of the output results for $O_2$, $CO_2$, $VO_2$, $VCO_2$, REE, and RQ compared to the reference method (FIGS. 16-18).

Stability of the Sensor Chip and Venturi Tube Flow Meter:

In regard to $O_2$ and $CO_2$ detection, the sensor chip of the present disclosure is highly stable for over a year stored at room temperature, and for over 2 years stored at lower temperatures. The high level of stability is provided by three main reasons: 1) packaging of the sensor chip in a dry and inert environment; 2) curing of the sensor chip with temperature-dependent process performed after fabrication; and 3) performing batch-to-batch calibration after production and using QR code to carry calibration factors for each individual sensor chip.

In regard to the stability of the Venturi tube flow meter, the flow calibration has demonstrated stability for 2 years and thousands of consecutives measurements performed without re-calibration. This performance avoids issues with instrument maintenance, currently present in metabolic devices, instruments and carts that need a calibration at least once a year (if not every time before use).

Figure 19:
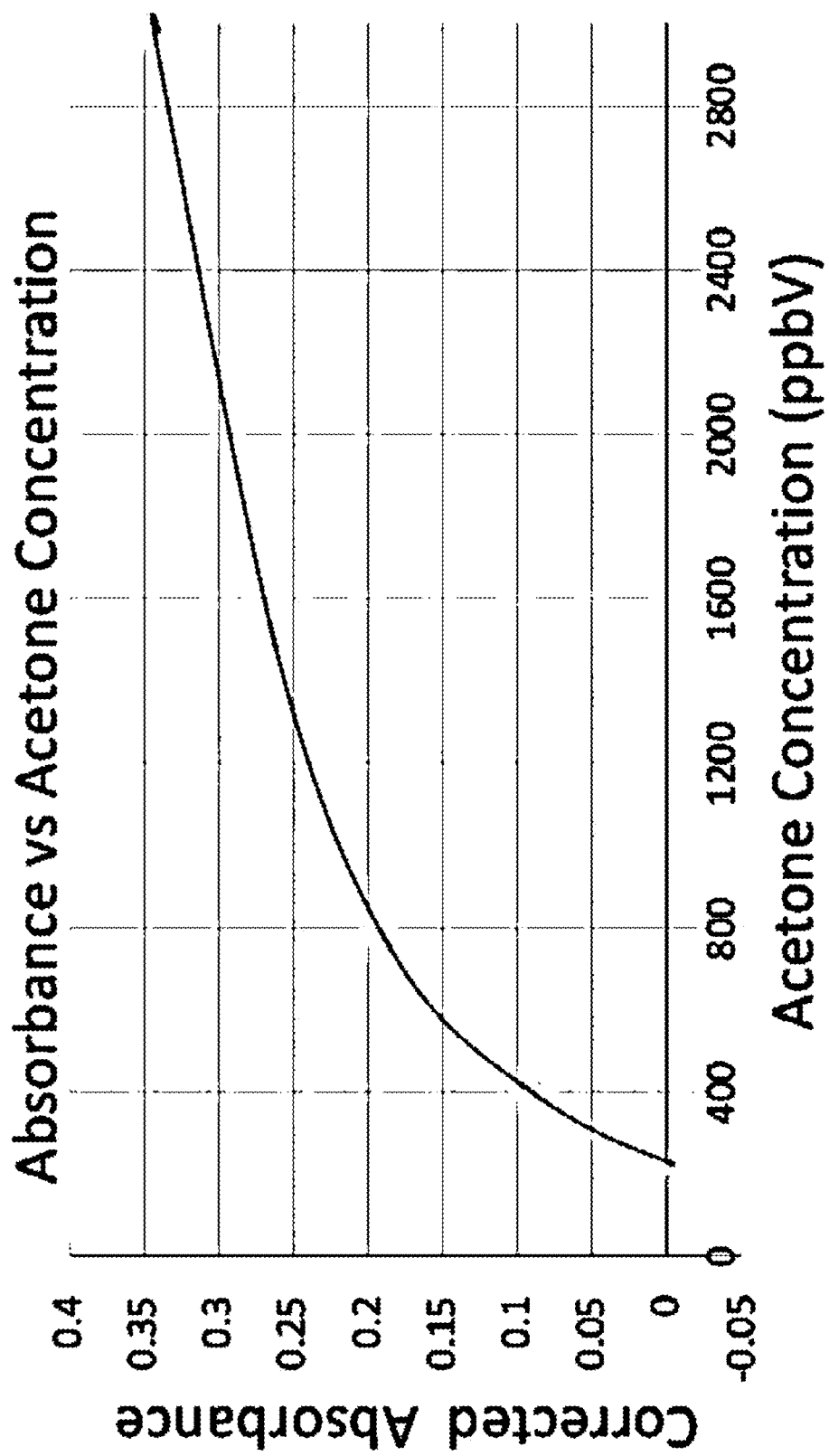
FIG. 19 shows example of an acetone reading measured by a self-contained wearable metabolic analyzer, including a chemical sensor in addition to $O_2$ and $CO_2$ sensors.

Detection of Other Analytes:

Referring now to FIG. 19, an example of an acetone reading measured by a self-contained wearable metabolic analyzer, including a chemical sensor in addition to $O_2$ and $CO_2$ sensors as shown. As previously mentioned, acetone is an indicator of fat oxidation and it is relevant to metrics of respiratory quotient. The parameter provides further information on whether the person sustains significant fat oxidation when levels are detected above the typical person's baseline level, typically between 200 ppb and 1 ppm level.

In one aspect the present disclosure describes a stand-alone (fully integrated) self-contained wearable metabolic analyzer, including miniaturized and light-weight sensors for simultaneous analysis of multiple metabolites (e.g., oxygen, carbon dioxide, and ketone), and detection of flow rate, temperature, humidity level of the breath, as well as orientation of the device for the metabolic rate, respiratory quotient and other metabolic related physiological parameter measurements.

In another aspect, the present disclosure features several innovative chemical sensing and engineering solutions that overcome the difficulties of known devices and to address the need for simultaneous detection of multiple metabolic parameters with a miniaturized and light-weight integrated wearable analyzer, eliminating burden of additional instruments, and addressing personal hygiene issues and ease of use. Conventional metabolic analyzers typically use electrochemical or fluorescence sensors for oxygen ($O_2$) detection, infrared sensor for carbon dioxide ($CO_2$) detection, and turbine, ultrasonic, or differential pressure sensors for flow rate measurement. These technologies are either too heavy or too bulky for an on-face self-contained wearable metabolic analyzer. A miniaturized integrated sensor unit is developed in the present disclosure to measure $O_2$ and $CO_2$ in breath and measure breath exhalation flow rate, along with breath temperature and humidity.

In one example, the apparatus disclosed here is a stand-alone, wearable, fully functional, and integrated metabolic analyzer in the shape of a mask for measuring of resting energy expenditure (REE), respiratory quotient (RQ), oxygen consumption rate ($VO_2$), carbon dioxide production rate ($VCO_2$), breath frequency (BF), and tidal volume (TV). The disclosure includes 1) a miniaturized, multiplexed, configurable colorimetric sensing module for breath $O_2$ and $CO_2$ detection (addressing size, weight, and cost); 2) a miniaturized Venturi tube and pressure sensor-based flow module for accurate and less obstructive breath flow rate monitoring (addressing comfort of use and accuracy); 3) a unit and method to compensate the pressure sensor signal drift due to movement and orientation change via a gyroscope or accelerometer built-in the device body (addressing ease of use); 4) a design of a virus/micro-organism free measurement mechanism with a disposable mask of easy assembly (addressing the hygiene issues); 5) inclusion of sensors to monitor ambient temperature, humidity, barometric pressure (for user's comfort climate measures and accuracy), as well as breath temperature for breath flow rate and volume correction (for accurate standardized measurements); 6) integration and assembly of the various components within a compact, light, weight-balanced, and stand-alone device body; 7) communication unit and method of the data collected by the sensors built in the device body with an external device (e.g., phone, tablet or computer), 8) software apps run on the external device for data transmission and management, and for human interface.

Although metabolic rate, RQ, and other physiological parameters derived from the measured $CO_2$, $O_2$, and flow rate are the primary parameters focused in this disclosure, a self-contained wearable metabolic analyzer can be configured and expanded for other healthcare applications, including, 1) detecting biomarkers in breath, such as, acetone ($CH_3COCH_3$), alcohol ($C_2H_5OH$), nitric oxide (NO), hydrogen ($H_2$), methane ($CH_4$), carbon monoxide (CO), ammonia ($NH_3$), and volatile organic compounds (VOCs) for detection of fat oxidation, inflammation, microbiome related gases, poisoning/smoking, esophagus or mouth bacterial infection, and other disease screening, diagnosis, and management; 2) detecting rebreathed carbon dioxide for assessing cardiac output, and stroke volume, 3) detecting forced pulmonary parameters for assessing lung functions (e.g. spirometry parameters in Chronic Obstructive Pulmonary Disease); or 4) measuring $VO_2$ max and lactate thresholds during exercise conditions for physical performance assessment.

Certain exemplary embodiments of the invention have been described herein in considerable detail in order to comply with the patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

What is claimed is:

1. A self-contained metabolic analysis apparatus configured to be worn by a user, the apparatus comprising:

a device body including (i) an integrated chemical sensor module comprising a colorimetric chemical sensor chip for simultaneous oxygen and carbon dioxide measurement, and (ii) a flow sensor module comprising a Venturi tube and a pressure sensor for exhaled breath flow rate measurement;

a disposable mask attached to the device body and configured to allow aseptic breathing according to which the user inhales ambient air through at least one inhalation one-way valve, and exhales breath through an exhalation one-way valve into the flow sensor module, from which a portion of the user's exhaled breath is taken into the chemical sensor module, wherein the exhalation one-way valve permits only exhaled breath flow to reach the Venturi tube;

headgear adapted to attach the device body to a head of the user; and a data transmission circuit configured for communication with an external electronic device;

wherein the Venturi tube includes a narrow constriction, a first opening located upstream of the narrow constriction, a second opening located proximate to the narrow constriction, and an outlet arranged to guide the portion of the user's exhaled breath to the integrated chemical sensor module; and wherein the pressure sensor is in sensory communication with the first and second openings of the Venturi tube, and the flow sensor module is configured to determine exhaled breath flow rate from output signals of the pressure sensor.

2. The apparatus of claim 1 wherein the integrated chemical sensor module further comprises:
a detection chamber including an inlet to guide the portion of the user's exhaled breath into the detection chamber, and an outlet to guide the portion of the user's exhaled breath out of the detection chamber;
a light emitting diode (LED) light source located on a first side of the detection chamber to illuminate the colorimetric chemical sensor chip;
a light detection unit located on a second side, opposite the first side, of the detection chamber to collect optical signals from the colorimetric chemical sensor chip; and
an electronic circuit configured to receive electronic signals from the light detection unit and determine optical absorbance at a single wavelength of light emitted by the LED light source for oxygen and carbon dioxide.

3. The apparatus of claim 1 wherein the flow sensor module further comprises:
a temperature sensor in sensory communication with the Venturi tube for breath temperature measurement.

4. The apparatus of claim 1 wherein the data transmission circuit is configured for wireless communication with the external electronic device, and the external electronic device is selected from the group consisting of a mobile phone, a tablet, a computer, and a printer with wireless capability.

5. The apparatus of claim 1, further comprising a Quick Response (QR) code in which calibration parameters of the colorimetric chemical sensor chip are encoded.

6. The apparatus of claim 1, wherein the at least one inhalation one-way valve comprises multiple inhalation one-way valves, and the disposable mask further comprises:
an exhalation port that includes the exhalation one-way valve, being located in a middle portion of the disposable mask; and
at least two inhalation ports each including a corresponding inhalation one-way valve of the multiple inhalation one-way valves,
wherein the exhalation port is arranged between the at least two inhalation ports.

7. The apparatus of claim 6 wherein the exhalation port has a diameter in a range of 20 mm to 40 mm.

8. The apparatus of claim 6 wherein the at least two inhalation ports have a combined cross-sectional area that is larger than a cross-sectional area of the exhalation port.

9. The apparatus of claim 1 wherein the integrated chemical sensor module has a geometry configured to promote mixing of the breath sample.

10. The apparatus of claim 1 wherein the device body further comprises a humidity sensor for monitoring ambient humidity level, and the apparatus is configured to use an output of the humidity sensor to compensate for ambient humidity in determining exhaled breath flow rate.

11. The apparatus of claim 1 wherein the device body further comprises a barometer, and the apparatus is configured to use an output of the barometer to compensate for ambient pressure in determining exhaled breath flow rate.

12. The apparatus of claim 1 wherein the device body further comprises a gyroscope for detecting an orientation of the device body during determination of breath flow rate.

13. The apparatus of claim 1 wherein the flow sensor module further comprises a barometer, a temperature sensor, and a converter adapted to convert a measured exhaled breath flow rate to a standard pressure and temperature condition using outputs from the barometer and temperature sensor.

14. The apparatus of claim 1 wherein the flowسensor module further comprises a gyroscope configured for detecting orientation of the device body and utilizes an error correction algorithm and data from the gyroscope to correct for an effect of gravity on the exhaled breath flow rate measurement utilizing a pressure sensor using the data from the gyroscope.

15. The apparatus of claim 1 wherein the Venturi tube has a diameter within a range of 3 mm to 25 mm at the narrowed constriction.

16. The apparatus of claim 1, being configured to determine oxygen consumption rate ($VO_2$) and carbon dioxide production rate ($VCO_2$) using the integrated chemical sensor module and the flow sensor module, and configured to determine resting energy expenditure (REE) using $VO_2$ and $VCO_2$ according to the Weir equation, and determine respiratory quotient (RQ).

17. The apparatus of claim 1, being configured to determine oxygen consumption rate ($VO_2$) using the integrated chemical sensor module and the flow sensor module, and configured to determine maximum oxygen consumption rate ($VO_2$ Max) from $VO_2$.

18. The apparatus of claim 1 wherein the colorimetric chemical sensor chip is configured to detect at least one chemical analyte selected from the group consisting of: acetone, alcohol, ammonia, hydrogen, methane, carbon monoxide, nitric oxide, and volatile organic compounds.

19. The apparatus of claim 1 wherein the colorimetric chemical sensor chip comprises an array of sensing areas including an oxygen sensing area, a carbon dioxide sensing area, and a reference correction sensing area.

20. A self-contained metabolic analysis apparatus configured to be worn by a user, the apparatus comprising:
a device body including (i) an integrated chemical sensor module comprising a colorimetric chemical sensor chip for simultaneous oxygen and carbon dioxide measurement, and (ii) a flow sensor module comprising a Venturi tube and a pressure sensor for exhaled breath flow rate measurement, wherein the pressure sensor is in sensory communication with Venturi tube, and the flow sensor module is configured to determine breath flow rate from output signals of the pressure sensor;
a disposable mask attached to the device body, the disposable mask including (a) an exhalation port comprising an exhalation one-way valve located in a middle portion of the disposable mask to allow at least a portion of the user's exhaled breath into the flow sensor module, from which a portion of the user's breath is passed into the integrated chemical sensor module, and (b) at least two inhalation ports each comprising an inhalation one-way valve, with the exhalation port being arranged between the at least two inhalation ports, the disposable mask being configured to allow breathing headgear adapted to attach the device body to a head of the user; and
a data transmission circuit configured for communication with an external electronic device.

* * * * *